US008285510B2

(12) United States Patent
Schowengerdt et al.

(10) Patent No.: US 8,285,510 B2
(45) Date of Patent: Oct. 9, 2012

(54) METHOD, APPARATUS, AND ARTICLE TO FACILITATE DISTRIBUTED EVALUATION OF OBJECTS USING ELECTROMAGNETIC ENERGY

(75) Inventors: Brian T. Schowengerdt, Seattle, WA (US); Thomas A. Furness, III, Seattle, WA (US); Nicholas E. Walker, Springfield, OR (US)

(73) Assignee: Visualant, Inc., Seattle, WA (US)

( * ) Notice: Subject to any disclaimer, the term of this patent is extended or adjusted under 35 U.S.C. 154(b) by 0 days.

(21) Appl. No.: 13/162,415

(22) Filed: Jun. 16, 2011

(65) Prior Publication Data
US 2011/0243571 A1 Oct. 6, 2011

Related U.S. Application Data

(63) Continuation of application No. 11/831,662, filed on Jul. 31, 2007, now Pat. No. 7,996,173.

(60) Provisional application No. 60/834,662, filed on Jul. 31, 2006.

(51) Int. Cl.
*G01P 21/00* (2006.01)
(52) U.S. Cl. ......... 702/108; 702/106; 702/189; 702/193
(58) Field of Classification Search .................. 356/320; 702/106, 108, 189, 193; 705/1, 34, 40
See application file for complete search history.

(56) References Cited

U.S. PATENT DOCUMENTS

| 3,499,158 A | 3/1970 | Lavine et al. ............... 250/217 |
| 3,504,164 A | 3/1970 | Farrell et al. ................ 235/150 |
| 3,582,659 A | 6/1971 | Dekker .................... 250/214 R |
| 3,679,449 A | 7/1972 | Nagot et al. ..................... 117/1 |
| 3,822,098 A | 7/1974 | Rudder et al. ................ 356/209 |
| 3,867,039 A | 2/1975 | Nelson ........................ 356/178 |
| 3,922,090 A | 11/1975 | Fain ............................. 356/71 |
| 3,942,185 A | 3/1976 | Lebailly ........................ 357/17 |
| 3,994,590 A | 11/1976 | Di Martini et al. ........... 356/178 |
| 4,082,188 A | 4/1978 | Grimmell et al. ............. 209/73 |
| 4,098,940 A | 7/1978 | Groh et al. .................... 428/218 |

(Continued)

FOREIGN PATENT DOCUMENTS
WO 91/05459 5/1991
(Continued)

OTHER PUBLICATIONS

CRi Nuance Multispectral Imaging System, URL=http://www.cri-inc.com/products/nuance.asp, download date Jan. 30, 2007, 2 pages.

(Continued)

*Primary Examiner* — Michael Nghiem
*Assistant Examiner* — Elias Desta
(74) *Attorney, Agent, or Firm* — Seed IP Law Group PLLC

(57) ABSTRACT

Objects such as manufactured goods or articles, works of art, media such as identity documents, legal documents, financial instruments, transaction cards, other documents, and/or biological tissue are sampled via sequential illumination in various bands of the electromagnetic spectrum, a test response to the illumination is analyzed with respect to reference responses of reference objects. The sequence may be varied. The sequence may define an activation order, a drive level and/or temperature for operating one or more sources. Illumination may be in visible, infrared, ultraviolet, or other portions of the electromagnetic spectrum. Elements of the evaluation system may be remote from one another, for example coupled by a network.

15 Claims, 21 Drawing Sheets

U.S. PATENT DOCUMENTS

| | | | |
|---|---|---|---|
| 4,120,445 A | 10/1978 | Carrier et al. | 229/53 |
| 4,183,989 A | 1/1980 | Tooth | 428/195 |
| 4,241,738 A | 12/1980 | Lübbers et al. | 128/666 |
| 4,277,514 A | 7/1981 | Sugiura et al. | 427/1 |
| 4,325,981 A | 4/1982 | Sugiura et al. | 427/7 |
| 4,652,913 A | 3/1987 | Saitoh et al. | 358/75 |
| 4,678,338 A | 7/1987 | Kitta et al. | 356/402 |
| 4,760,250 A | 7/1988 | Loeppert | 250/227 |
| 4,830,501 A | 5/1989 | Terashita | 356/402 |
| 4,921,278 A | 5/1990 | Shiang et al. | 283/87 |
| 4,952,061 A | 8/1990 | Edgar | 356/407 |
| 5,137,364 A | 8/1992 | McCarthy | 356/402 |
| 5,325,167 A | 6/1994 | Melen | 356/71 |
| 5,377,000 A | 12/1994 | Berends | 356/73 |
| 5,576,627 A * | 11/1996 | McEwan | 324/639 |
| 5,619,326 A | 4/1997 | Takamatsu et al. | 356/357 |
| 5,844,680 A | 12/1998 | Sperling | 356/303 |
| 5,933,244 A | 8/1999 | Kiritchenko | 356/402 |
| 5,966,217 A | 10/1999 | Roe et al. | 356/402 |
| 6,020,583 A | 2/2000 | Walowit et al. | 250/226 |
| 6,035,246 A | 3/2000 | Wagner | 700/266 |
| 6,038,024 A | 3/2000 | Berner | 356/326 |
| 6,054,021 A | 4/2000 | Kurrle et al. | 162/140 |
| 6,165,609 A | 12/2000 | Curatolo | 428/343 |
| 6,172,745 B1 | 1/2001 | Voser et al. | 356/71 |
| 6,176,522 B1 | 1/2001 | Jackson | 283/91 |
| 6,255,948 B1 | 7/2001 | Wolpert et al. | 340/572.8 |
| 6,384,918 B1 | 5/2002 | Hubble, III et al. | 356/402 |
| 6,421,553 B1 | 7/2002 | Costa et al. | 600/476 |
| 6,449,045 B1 | 9/2002 | Mestha | 356/402 |
| 6,556,932 B1 | 4/2003 | Mestha et al. | 702/76 |
| 6,560,546 B1 | 5/2003 | Shenk et al. | 702/30 |
| 6,584,435 B2 | 6/2003 | Mestha et al. | 702/196 |
| 6,621,576 B2 | 9/2003 | Tandon et al. | 356/320 |
| 6,633,382 B2 | 10/2003 | Hubble, III et al. | 356/402 |
| 6,639,699 B2 | 10/2003 | Matsuyama | 359/35 |
| 6,690,465 B2 | 2/2004 | Shimizu et al. | 356/326 |
| 6,718,046 B2 | 4/2004 | Reed et al. | 382/100 |
| 6,721,440 B2 | 4/2004 | Reed et al. | 382/100 |
| 6,721,629 B2 | 4/2004 | Wendling et al. | 700/279 |
| 6,724,912 B1 | 4/2004 | Carr et al. | 382/100 |
| 6,731,785 B1 | 5/2004 | Mennie et al. | 382/135 |
| 6,744,909 B1 | 6/2004 | Kostrzewski et al. | 382/115 |
| 6,748,533 B1 | 6/2004 | Wu et al. | 713/176 |
| 6,757,406 B2 | 6/2004 | Rhoads | 382/100 |
| 6,763,124 B2 | 7/2004 | Alattar et al. | 382/100 |
| 6,782,115 B2 | 8/2004 | Decker et al. | 382/100 |
| 6,788,800 B1 | 9/2004 | Carr et al. | 382/100 |
| 6,798,517 B2 | 9/2004 | Wagner et al. | 356/406 |
| 6,804,377 B2 | 10/2004 | Reed et al. | 382/100 |
| 6,888,633 B2 | 5/2005 | Vander Jagt et al. | 356/407 |
| 6,930,773 B2 | 8/2005 | Cronin et al. | 356/300 |
| 6,937,323 B2 | 8/2005 | Worthington et al. | 356/73 |
| 6,968,337 B2 | 11/2005 | Wold | 707/100 |
| 6,992,775 B2 | 1/2006 | Soliz et al. | 356/456 |
| 6,993,535 B2 | 1/2006 | Bolle et al. | 707/104 |
| 6,995,839 B1 | 2/2006 | Shapiro | 356/301 |
| 6,996,478 B2 | 2/2006 | Sunshine et al. | 702/22 |
| 7,001,038 B2 | 2/2006 | Bock et al. | 362/125 |
| 7,003,132 B2 | 2/2006 | Rhoads | 382/100 |
| 7,003,141 B1 | 2/2006 | Lichtermann et al. | 382/124 |
| 7,005,661 B2 | 2/2006 | Yamaguchi et al. | 250/559.16 |
| 7,006,204 B2 | 2/2006 | Coombs et al. | 356/71 |
| 7,008,795 B2 | 3/2006 | Yerazunis et al. | 436/164 |
| 7,012,695 B2 | 3/2006 | Maier et al. | 356/453 |
| 7,016,717 B2 | 3/2006 | Demos et al. | 600/473 |
| 7,018,204 B2 | 3/2006 | Jung et al. | 433/26 |
| 7,023,545 B2 | 4/2006 | Slater | 356/73 |
| 7,026,600 B2 | 4/2006 | Jamieson et al. | 250/221 |
| 7,027,134 B1 | 4/2006 | Garcia-Rubio et al. | 356/39 |
| 7,027,165 B2 | 4/2006 | De Haas et al. | 356/600 |
| 7,027,619 B2 | 4/2006 | Pavlidis et al. | 382/115 |
| 7,031,555 B2 | 4/2006 | Troyanker | 382/305 |
| 7,032,988 B2 | 4/2006 | Darby et al. | 347/14 |
| 7,035,873 B2 | 4/2006 | Weare | 707/104.1 |
| 7,038,766 B2 | 5/2006 | Kerns et al. | 356/71 |
| 7,041,362 B2 | 5/2006 | Barbera-Guillem | 428/206 |
| 7,044,386 B2 | 5/2006 | Berson | 235/491 |
| 7,046,346 B2 | 5/2006 | Premjeyanth et al. | 356/71 |
| 7,046,842 B2 | 5/2006 | Lin et al. | 382/165 |
| 7,049,597 B2 | 5/2006 | Bodkin | 250/353 |
| 7,052,730 B2 | 5/2006 | Patel et al. | 427/7 |
| 7,052,920 B2 | 5/2006 | Ushio et al. | 438/14 |
| 7,058,200 B2 | 6/2006 | Donescu et al. | 382/100 |
| 7,061,652 B2 | 6/2006 | Kurita et al. | 358/3.28 |
| 7,063,260 B2 | 6/2006 | Mossberg et al. | 235/454 |
| 7,170,606 B2 | 1/2007 | Yerazunis | 356/432 |
| 7,171,680 B2 | 1/2007 | Lange | 726/5 |
| 7,252,241 B2 * | 8/2007 | Yamada | 235/492 |
| 7,259,853 B2 | 8/2007 | Hubble, III et al. | 356/402 |
| 7,307,752 B1 | 12/2007 | Mestha et al. | 358/1.9 |
| 7,383,261 B2 | 6/2008 | Mestha et al. | 707/7 |
| 7,570,988 B2 | 8/2009 | Ramanujam et al. | 600/476 |
| 7,996,173 B2 * | 8/2011 | Schowengerdt et al. | 702/108 |
| 2002/0009213 A1 | 1/2002 | Rowe et al. | 382/115 |
| 2002/0012447 A1 | 1/2002 | Amidror et al. | 382/100 |
| 2002/0146146 A1 | 10/2002 | Miolla et al. | 382/100 |
| 2002/0176600 A1 | 11/2002 | Rhoads et al. | 382/100 |
| 2003/0031347 A1 | 2/2003 | Wang | 382/115 |
| 2003/0063772 A1 | 4/2003 | Smith et al. | 382/100 |
| 2003/0095726 A1 | 5/2003 | Kia et al. | 382/313 |
| 2003/0142314 A1 | 7/2003 | Hubble, III et al. | 356/402 |
| 2003/0151611 A1 | 8/2003 | Turpin et al. | 345/589 |
| 2003/0152274 A1 | 8/2003 | McGrew | 382/210 |
| 2003/0156752 A1 | 8/2003 | Turpin et al. | 382/162 |
| 2003/0158617 A1 | 8/2003 | Turpin et al. | 700/97 |
| 2003/0158788 A1 | 8/2003 | Turpin et al. | 705/26 |
| 2003/0174882 A1 | 9/2003 | Turpin et al. | 382/162 |
| 2003/0210805 A1 | 11/2003 | Lofgren et al. | 382/100 |
| 2004/0005086 A1 | 1/2004 | Wolff et al. | 382/118 |
| 2004/0071311 A1 | 4/2004 | Choi et al. | 382/100 |
| 2004/0071366 A1 | 4/2004 | Zhang et al. | 382/284 |
| 2004/0091131 A1 | 5/2004 | Honsinger et al. | 382/100 |
| 2004/0091153 A1 | 5/2004 | Nakano et al. | 382/228 |
| 2004/0101158 A1 | 5/2004 | Butler | 382/100 |
| 2004/0101159 A1 | 5/2004 | Butler | 382/100 |
| 2004/0101168 A1 | 5/2004 | Kostrzewski et al. | 382/115 |
| 2004/0105569 A1 | 6/2004 | Sharma et al. | 382/100 |
| 2004/0119976 A1 | 6/2004 | Faupel et al. | 356/337 |
| 2006/0059013 A1 | 3/2006 | Lowe | 705/2 |
| 2006/0132790 A1 | 6/2006 | Gutin | 356/479 |
| 2006/0161788 A1 * | 7/2006 | Turpin et al. | 713/186 |
| 2006/0247532 A1 | 11/2006 | Ramanujam et al. | 600/476 |
| 2007/0078610 A1 | 4/2007 | Adams et al. | 702/28 |
| 2008/0171925 A1 | 7/2008 | Xu et al. | 600/316 |
| 2009/0112101 A1 | 4/2009 | Furness, III et al. | 600/477 |

FOREIGN PATENT DOCUMENTS

| | | |
|---|---|---|
| WO | 03/069884 | 8/2003 |
| WO | 2006050367 | 5/2006 |
| WO | 2008016590 | 2/2008 |

OTHER PUBLICATIONS

CRi Products Components, URL=http://www.cri-inc.com/products/components.asp, download date Jan. 30, 2007, 5 pages.

Furness III et al., "Method, Apparatus, and Article to Facilitate Evaluation of Objects Using Electromagnetic Energy," U.S. Appl. No. 60/834,589, filed Jul. 31, 2006, 135 pages.

Furness III et al., "Method, Apparatus, and Article to Facilitate Evaluation of Objects Using Electromagnetic Energy," U.S. Appl. No. 60/871,639, filed Dec. 22, 2006, 140 pages.

Furness III et al., "Method, Apparatus, and Article to Facilitate Evaluation of Objects Using Electromagnetic Energy," U.S. Appl. No. 60/883,312, filed Jan. 3, 2007, 147 pages.

Furness III et al., "Method, Apparatus, and Article to Facilitate Evaluation of Objects Using Electromagnetic Energy," U.S. Appl. No. 60/890,446, filed Feb. 16, 2007, 155 pages.

Furness III et al., "Method, Apparatus, and Article to Facilitate Evaluation of Objects Using Electromagnetic Energy," U.S. Appl. No. 11/831,717, filed Jul. 31, 2007 156 pages.

Furness III et al., "Method, Apparatus, and Article to Facilitate Evaluation of Objects Using Electromagnetic Energy," Preliminary Amendment filed Jan. 9, 2009 for U.S. Appl. No. 11/831,717, 39 pages.

International Search Report, mailed Jun. 21, 2007, for PCT/US2005/039495, 1 page.

International Search Report, mailed Jul. 23, 2008, for PCT/US2007/017082, 1 page.

Schowengerdt et al., "System and Method of Evaluating an Object Using Electromagnetic Energy," U.S. Appl. No. 60/820,938, filed Jul. 31, 2006, 69 pages.

Schowengerdt, B., "Brief Technical Description of the Cyclops Spectral Analysis and Authentication System," Visualant Inc. memorandum, not disclosed prior to Dec. 22, 2006, 2 pages.

Schowengerdt et al., "System and Method of Evaluating an Object Using Electromagnetic Energy," U.S. Appl. No. 12/375,814, filed Jan. 30, 2009, 69 pages.

Schowengerdt et al., "System and Method of Evaluating an Object Using Electromagnetic Energy," Preliminary Amendment filed Jan. 30, 2009 for U.S. Appl. No. 12/375,814, 14 pages.

Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.

Thomas, R., "A Beginner's Guide to ICP-MS—Part V: The Ion Focusing System,"Spectrospcopy 16(9):38-44, Sep. 2001. (Blank pages appear to be intentional).

Turpin, K., "Full Color Spectrum Object Authentication Methods and Systems," U.S. Appl. No. 60/623,881, filed Nov. 1, 2004, 114 pages.

Turpin et al., "Full Color Spectrum Object Authentication Methods and Systems," U.S. Appl. No. 60/732,163, filed Oct. 31, 2005, 198 pages.

Turpin et al., "Full Color Spectrum Object Authentication Methods and Systems," U.S. Appl. No. 11/264,626, filed Nov. 1, 2005, 46 pages.

Turpin et al., "Full Color Spectrum Object Authentication Methods and Systems," Preliminary Amendment filed Jul. 27, 2006 for U.S. Appl. No. 11/264,626, 3 pages.

Turpin et al., "Full Color Spectrum Object Authentication Methods and Systems," Office Action mailed May 4, 2007 for U.S. Appl. No. 11/264,626, 9 pages.

Vrhel, "An LED based spectrophotometric instrument," *Color Imaging: Device-Independent Color, Color Hardcopy, and Graphic Arts IV, Proceedings of the SPIE 3648*:226-236, Jan. 1999.

"Color Technology Beyond the Visible Spectrum Creating Solutions for Product Authentication: Extraordinary Investment Opportunity & 12 Month Roadmap," Visualant Inc., Seattle, Washington, Nov. 17, 2006, 10 pages.

Written Opinion, mailed Jun. 21, 2007, for PCT/US2005/039495, 5 pages.

Written Opinion, mailed Jul. 23, 2008, for PCT/US2007/017082, 3 pages.

Schowengerdt et al., "Method, Apparatus, and Article to Facilitate Distributed Evaluation of Objects Using Electromagnetic Energy," Office Action mailed Jan. 21, 2010 for U.S. Appl. No. 11/831,662, 21 pages.

Schowengerdt et al., "Method, Apparatus, and Article to Facilitate Distributed Evaluation of Objects Using Electromagnetic Energy," Amendment filed Apr. 26, 2010 for U.S. Appl. No. 11/831,662, 41 pages.

Schowengerdt et al., "Method, Apparatus, and Article to Facilitate Distributed Evaluation of Objects Using Electromagnetic Energy," Office Action mailed Jul. 8, 2010 for U.S. Appl. No. 11/831,662, 11 pages.

Schowengerdt et al., "Method, Apparatus, and Article to Facilitate Distributed Evaluation of Objects Using Electromagnetic Energy," Amendment filed Oct. 8, 2010 for U.S. Appl. No. 11/831,662, 19 pages.

Schowengerdt et al., "Method, Apparatus, and Article to Facilitate Distributed Evaluation of Objects Using Electromagnetic Energy," Office Action mailed Dec. 22, 2010 for U.S. Appl. No. 11/831,662, 16 pages.

Schowengerdt et al., "Method, Apparatus, and Article to Facilitate Distributed Evaluation of Objects Using Electromagnetic Energy," Response filed Feb. 22, 2011 for U.S. Appl. No. 11/831,662, 4 pages.

Furness III et al., "Method, Apparatus, and Article to Facilitate Evaluation of Objects Using Electromagnetic Energy," Office Action mailed Feb. 28, 2011 for U.S. Appl. No. 11/831,717, 10 pages.

Furness III et al., "Method, Apparatus, and Article to Facilitate Evaluation of Objects Using Electromagnetic Energy," Amendment filed Jul. 28, 2011 for U.S. Appl. No. 11/831,717, 32 pages.

* cited by examiner

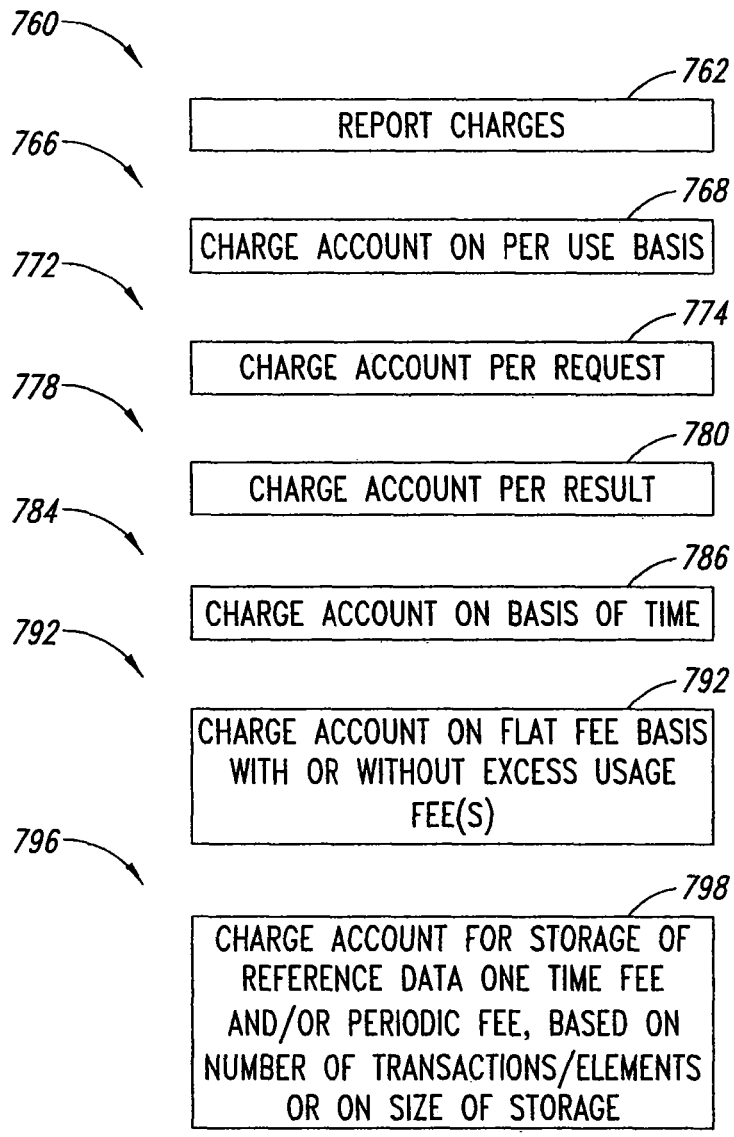

METHOD, APPARATUS, AND ARTICLE TO FACILITATE DISTRIBUTED EVALUATION OF OBJECTS USING ELECTROMAGNETIC ENERGY

CROSS-REFERENCE TO RELATED APPLICATIONS

This application is a continuation of U.S. patent application Ser. No. 11/831,662, filed Jul. 31, 2007, now U.S. Pat. No. 7,996,173, which claims benefit under 35 U.S.C. §119(e) to U.S. Provisional Patent Application No. 60/834,662, filed Jul. 31, 2006, each of which are incorporated herein by reference in their entirety.

BACKGROUND OF THE INVENTION

1. Field of the Invention

This disclosure generally relates to evaluation systems, and more particularly to systems that evaluate characteristics of an object using electromagnetic energy.

2. Description of the Related Art

There are a number of proposed systems that employ spectral analysis of light received from a sample to recognize the sample.

US Patent Application Publication 2006-0161788 A1 describes full color spectrum object authentication methods and systems. In particular, a spectrum measuring device measures a region of respective sampled objects to produce spectral content information that identifies the sampled objects. The spectrum measuring device includes a plurality of individual sensors, which preferably includes specialized narrow band near-infrared and near-ultraviolet sensors, for example photodiodes or photomultipliers. Computers employ spectral analysis software to generate a unique measured pattern, which is then compared with reference patterns stored in a database. The spectral analysis software may be remotely located on a server accessible by the computers. The spectral analysis is preferably performed using XYZ color space modeling, although other color space models may be employed. The region being sampled may be varied to prevent third parties from easily anticipating the location. Samples may be take from multiple regions to insure accuracy.

U.S. Pat. No. 5,844,680 is directed to a device and process for measuring and analyzing spectral radiation, in particular for measuring and analyzing color characteristics. In particular, a number of radiation sources are provided in combination with a sensor for detecting radiation within a desired wavelength range. The radiation sources have spectral characteristics that are linearly independent from one another, but overlap so that in combination, the radiation sources generate radiation over the entire desired wavelength range. Alternatively, a single radiation source is provided that generates radiation over the entire desired wavelength range, in combination with a plurality of sensors that have spectral sensing characteristics that are linearly independent from one another, but overlap the entire desired wavelength range. A control unit stores a number of calibration functions with linearly independent spectral characteristics.

The patents and other publications directed to the field of object authentication and/or object identification are too numerous to describe. The above described publication and patent are only representative.

BRIEF SUMMARY

It may be useful to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object. In order to uniquely identify a large number of objects, it may be useful to capture a large number of distinct reference responses from one or more reference objects. This may be difficult to do with fixed illumination. This may also be difficult to do when sensing at a limited number of bands. It may also be useful to separate hardware and/or software functions into separate systems that may be remote to one another. Such may reduce costs and/or permit the use of hardware or software that could not otherwise be financially justified. It may also be useful to apply the object evaluation to specific applications, for example: manufacturing process control, quality assurance, media authentication, biological tissue recognition, identification, verification, authentication, classification, and/or diagnostics.

In one aspect, a method of facilitating object testing includes operating at least one source at a test device according to a first sequence during a first period to emit electromagnetic energy in a plurality of bands, capturing electromagnetic energy returned to the test device during the first period, operating the at least one source at the test device according to a second sequence during a second period to emit electromagnetic energy in a plurality of bands, the second sequence different from the first sequence, capturing electromagnetic energy returned to the test device during the second period, and transmitting signals indicative of the captured electromagnetic energy remotely.

In another aspect, a method of facilitating responses to object testing requests includes storing a set of reference data representing responses of various reference objects to at least one sequence of illumination with a plurality of bands of electromagnetic energy, receiving a request from a remote test device including test data representing at least one response of an object being tested to at least a first sequence of illumination with the plurality of bands of electromagnetic energy, comparing the test data to the reference data, determining a result based on the comparing of the test data to the reference data, and tracking usage by a billing entity financially associated with the remote test device.

In another aspect, a method of facilitating remote testing of objects includes receiving a set of reference data from a remote entity, the set of reference data representing reference responses of various reference objects to at least one sequence of illumination with electromagnetic energy by a plurality of illumination sources, locally storing the received set of reference data, and providing remote access to the locally stored set of reference data on a fee basis.

In yet another aspect, a method of facilitating testing includes at a testing device, downloading a first subset of reference data at a first time from a remote set of reference data that is remote with respect to the testing device, at the testing device, operating at least one source according to a first sequence during a first period to emit electromagnetic energy in a plurality of bands, at the testing device, capturing electromagnetic energy returned during the first period, at the testing device, comparing the captured electromagnetic energy to at least a portion of the subset of reference data, and at the local testing device, determining a result based on the comparing of the test data to the first subset of reference data.

In still yet another aspect, a method of facilitating evaluation of objects using electromagnetic energy includes determining a plurality of responses by at least one reference object to respective ones of a plurality of bands of electromagnetic radiation, and storing the determined responses by the at least one reference object to the respective ones of the plurality of bands of electromagnetic radiation in a computer-readable medium.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 17 is a flow diagram showing a method of reporting financial charges to a financial entity, according to one illustrated embodiment.

FIG. 18 is a flow diagram showing a method of executing a financial transaction, according to one illustrated embodiment.

FIG. 19 is a flow diagram showing a method of executing a financial transaction, according to another illustrated embodiment.

FIG. 20 is a flow diagram showing a method of executing a financial transaction, according to yet another illustrated embodiment.

FIG. 21 is a flow diagram showing a method of executing a financial transaction, according to still another illustrated embodiment.

FIG. 22 is a flow diagram showing a method of executing a financial transaction, according to further illustrated embodiment.

FIG. 23 is a flow diagram showing a method of executing a financial transaction, according to yet a further illustrated embodiment.

DETAILED DESCRIPTION OF THE INVENTION

Figure 1:
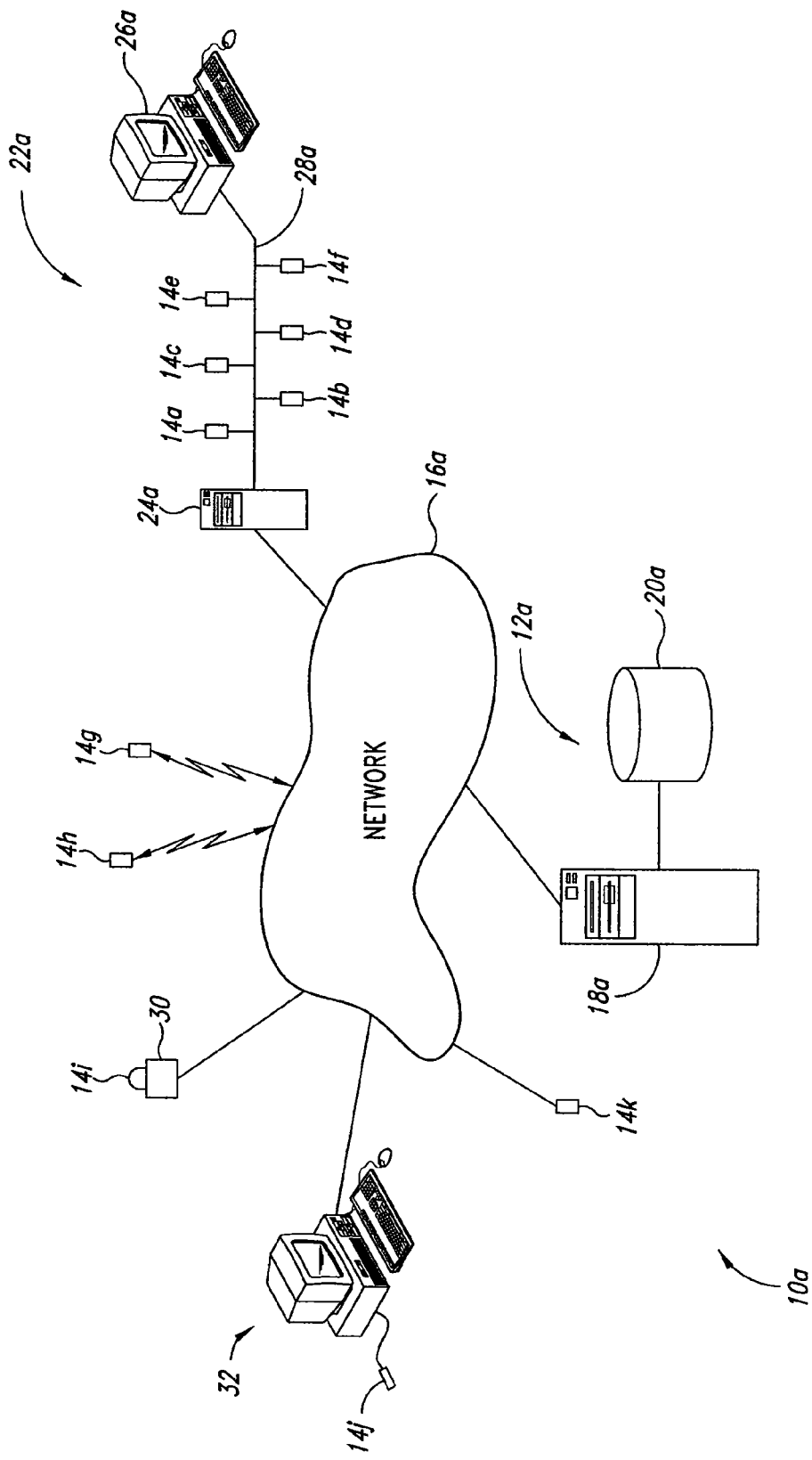
FIG. 1 is a schematic diagram of an object evaluation system including a host system and a plurality of remote test devices, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, networks, servers, microprocessors, memories, buses, and sources of electromagnetic energy have not been shown or described in detail to avoid unnecessarily obscuring descriptions of the embodiments.

Unless the context requires otherwise, throughout the specification and claims which follow, the word "comprise"

and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to recognize, identify, verify, authenticate and/or classify objects has numerous commercial applications.

It may be useful to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object.

For example, it may be useful to determine whether a manufactured object is identical to a previously evaluated manufactured object. Such may be useful in authenticating goods, and deterring counterfeiting or gray marketing of goods. For example, it may also be useful to determine whether other objects, such as paintings or other works of art are identical to a previously sampled work of art. For example, it may be useful to determine whether an object being manufactured is similar to a previously evaluated object. Such may be useful in manufacturing process control and/or quality control.

For example, it may be useful to determine whether a medium is identical to a previously evaluated medium. For example, it may be useful to determine whether a medium is similar to a previously evaluated medium.

For example, it may be useful to determine whether a medium such as a document is identical to a previously evaluated document. For example, it may be useful to determine whether a medium such as a document is similar to a previously evaluated document. Such may be useful in recognizing, identifying, verifying, authenticating and/or classifying financial instruments such as currency, checks, bonds, money orders, and/or securities. Such may also be useful in recognizing, identifying, verifying, authenticating and/or classifying identification documents, such as passports, identity cards (e.g., national, state, provincial, military, employer, school, organization), driver's licenses, and/or birth or naturalization certificates. Such may also be useful in recognizing, identifying, verifying, authenticating and/or classifying legal documents such as licenses, permits, assignments, deeds, wills, declarations, oaths, agreements, pleadings, or motions. Such may be useful in recognizing, identifying, verifying, authenticating and/or classifying medical related documents, such as medical records, medical data, medical reports, and/or medical images (e.g., X-Ray, CAT scan, MRI, tomography, etc.).

For example, it may also be useful to determine whether a medium such as a financial transaction card is identical to a previously evaluated financial transaction cards. For example, it may be useful to determine whether medium such as a financial transaction card is similar to a previously evaluated financial transaction card. Such may be useful in deterring fraud and/or misuse of documents and other media. Such may be useful in recognizing, identifying, verifying, authenticating and/or classifying financial instruments such as credit cards, debit cards, and/or gift cards.

Also for example, it may be useful to determine whether a piece of biological tissue from a subject is identical to a previously evaluated piece of tissue. Also for example, it may be useful to determine whether a piece of biological tissue from a subject is similar to a previously evaluated piece of tissue. Such may also be useful in recognizing, identifying, verifying, authenticating, classifying, and/or diagnosing biological tissue, such as bodily tissue including retinal tissue, skin, blood, bone, hair, organs, etc. For example, such may be used to identify a subject from which the biological tissue was obtained. Also for example, such may be used to assess a condition of the biological tissue or subject from which the biological tissue was obtained. For example, the biological tissue being evaluated may be compared to normal and/or abnormal reference biological tissue specimens, which may be used for diagnosing a condition.

It may be particularly useful where the above may occur based on the natural conditions or attributes of the object, media, or biological tissue, without the need to apply dedicated indicia such as serial numbers, machine-readable symbols (e.g., barcode symbols, area or matrix code symbols, stack code symbols), and/or radio frequency identification (RFID tags). Such dedicated data carriers may, in some embodiments, provide additional information regarding the object.

All of the above may, or may not, employ additional information about the object to facilitate the process. Additional information may include one or more measurable or observable physical characteristics of the object, media or biological tissue, for example, height, weight, age, hair or eye color, gender, location, type, size, denomination, serial numbers, security features, name, type, serial numbers, date of issue, color, etc. Such additional information may be employed to confirm a match, or to reduce the number of reference responses for comparison with a test response.

The ability to perform such in a network environment may provide a variety of distinct advantages. For example, such may make possible low cost end user test devices, which share or gain remote access to higher cost computing hardware and software. Such may allow the costs of the computing hardware and software to be shared over a variety of end users or financial entities. Such may also allow for "centralization" of relatively higher cost computing hardware and software, perhaps permitting use of high speed super-computers that could not otherwise be financially justified for individual end users or small groups of end users. Such also may allow for "decentralization" of low cost sampling or test devices. Such may also allow for light weight and/or low power consuming test devices. Such may additionally or alternatively permit the upgrade of previously distributed test devices. Such may also permit the distribution of work load. Such may also facilitate the backing up of data, and provide for redundancy. Other advantages will be apparent from the teachings herein.

FIG. 1 shows an object evaluation system 10a including one or more host systems 12a and a number of test devices 14a-14j (collectively 14) communicatively coupled to the host system 12a via one or more networks 16a. One or more of the test devices 14 may be remotely located with respect to the host system 12a.

The host system 12 may include one or more computing systems 18a and one or more storage devices or databases 20a. The computing system 18a may take any of a variety of forms, for example, personal computers, mini-computers, work stations, or main frame computers. The computing system 18a may, for example, take the form of a server computer executing server software. The storage or database 20a can take a variety of forms, including one or more hard disks or RAID drives, CD/ROMs, or other mass storage devices.

As discussed in detail below, the test devices 14 are operable to sequentially illuminate an object with a number of bands of electromagnetic energy. The test devices 14 are also operable to detect, measure or otherwise capture electromagnetic energy reflected, emitted, fluoresced, refracted, diffracted or otherwise transmitted, or otherwise returned from the object in response to the illumination. As used herein and in the claims, the terms illuminate, illuminates, illumination, and variations of such terms mean to expose to or reveal by the use of electromagnetic energy or electromagnetic radiation, whether in the visible portion of the electromagnetic spectrum, the optical portion (e.g., visible, near-infrared, near-ultraviolet), or other portions (e.g., far-infrared, far-ultraviolet, microwave, X-ray, etc.).

The network 16a can take a variety of forms, for example one or more local area networks (LANs), wide area networks (WANs), wireless LANs (WLANs), and/or wireless WANs (WWANs). The network 16a may employ packet switching or any other type of transmission protocol. The network 16a may, for example, take the form of the Internet or Worldwide Web portion of the Internet. The network 16a may take the form of public switched telephone network (PSTN) or any combination of the above, or other networks.

A number of the test devices 14a-14f may be logically or physically coupled as a test device system 22a. The test device system 22a may, for example, be associated with a single financial entity such as a business (e.g., corporation, partnership, sole proprietorship, limited liability company), a division of a business, a non-profit, a government (e.g., federal, state or provincial, county or parish, city or town), or division of a government (e.g., agency, department).

The test device system 22a may include one or more server computer systems 24a, and/or one or more personal computing systems 26a, all coupled by a network 28a. The network 28a may take the form of one or more local area networks (LAN) or wide area networks (WAN) and may or may not include wired or wireless access. The network 28a may take the form of an intranet, being restricted to a company or other financial entity. The test device system 22 may, for example, be affiliated with a particular company or financial entity.

A number of the test devices 14g-14h may be wirelessly coupled to the network 16a. One or more of the remote test devices 14i may be coupled to the network 16a via a cradle or other receiver 30. One or more of the test devices 14j may be coupled to the network 16a via a conventional communications interface, for example a USB port of a conventional computing system 32. One or more of the remote test devices 14k may be coupled to the network 16a via a wired connection. For example, the test device 14k may include an integrated phone modem allowing the test device 14k to call into the network 16a.

Figure 2:
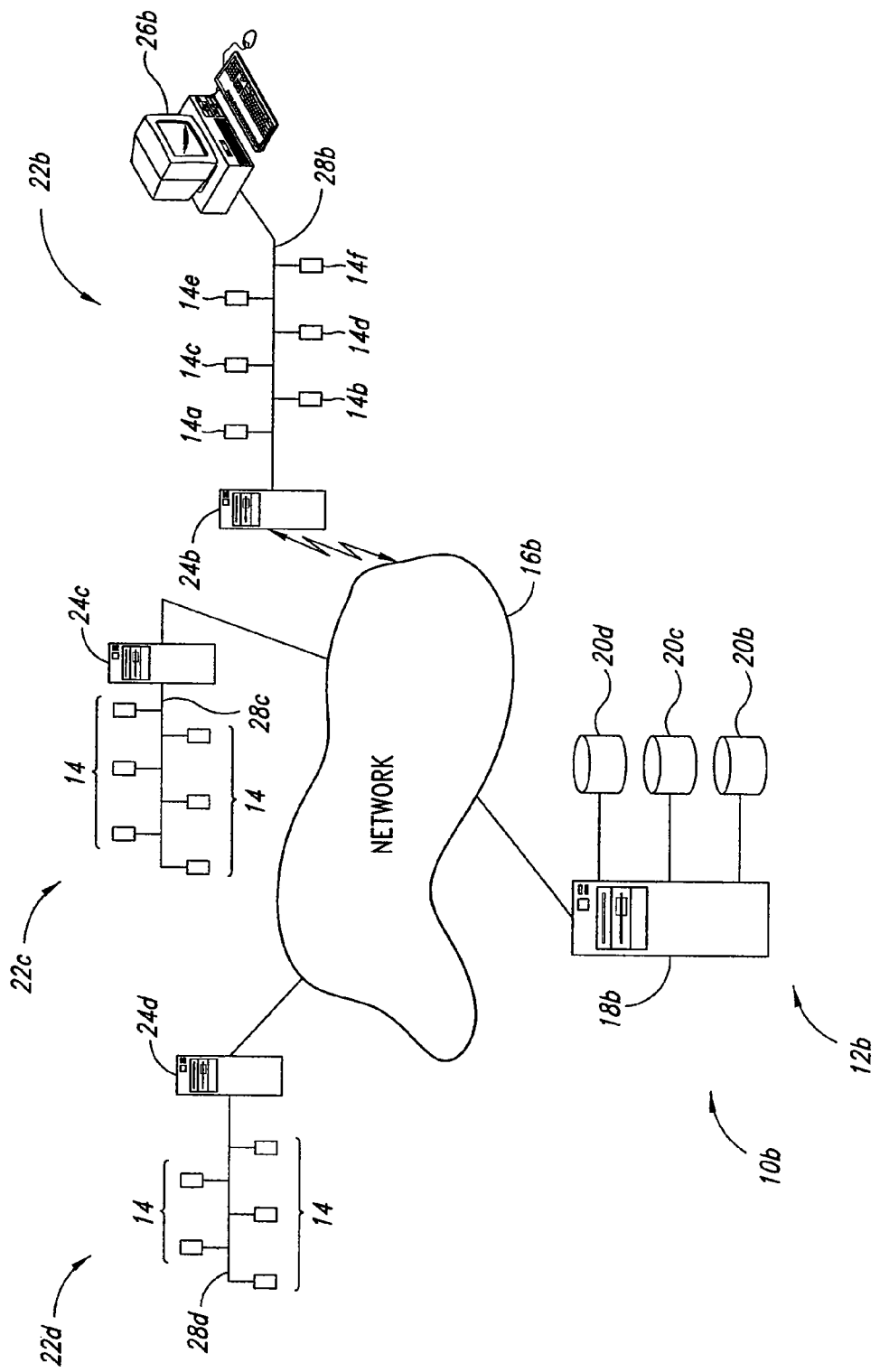
FIG. 2 is a schematic diagram of an object evaluation system including a host system with a plurality of databases associated with respective financial entities, and a plurality of remote test systems, according to another illustrated embodiment.

FIG. 2 shows an object evaluation system 10b according to another illustrated embodiment.

The object evaluation system 10b includes a number of distinct test device systems 22b-22d (collectively 22). The test device systems 22b-22d employ respective networking systems, for example, server computing systems 24b-24d and networks 28b-28d, respectively, to provide communication with the test devices 14. The test device systems 22b-22d may be similar to, or different from, the test device system 22a (FIG. 1) Each of the test device systems 22b-22d may, for example, be associated with a single financial entity such as a business (e.g., corporation, partnership, sole proprietorship, limited liability company), a division of a business, a non-profit, a government (e.g., federal, state or provincial, county or parish, city or town), or division of a government (e.g., agency, department). Some of the test device systems 22c-22d may include a wired connection to the network 16a, while other of the test device systems 22b may include a wireless connection to the network 16a.

The object evaluation system 10b includes one or more host systems 12b. The host system 12b includes one or more computing systems 18b, and a number of distinct storage or databases 20b-20d each associated with a respective financial entity or a respective one of the test device systems 22b-22d, respectively. The computing systems 18b are communicatively coupled to the test device systems 22b-22d via the network 16b.

Figure 3:
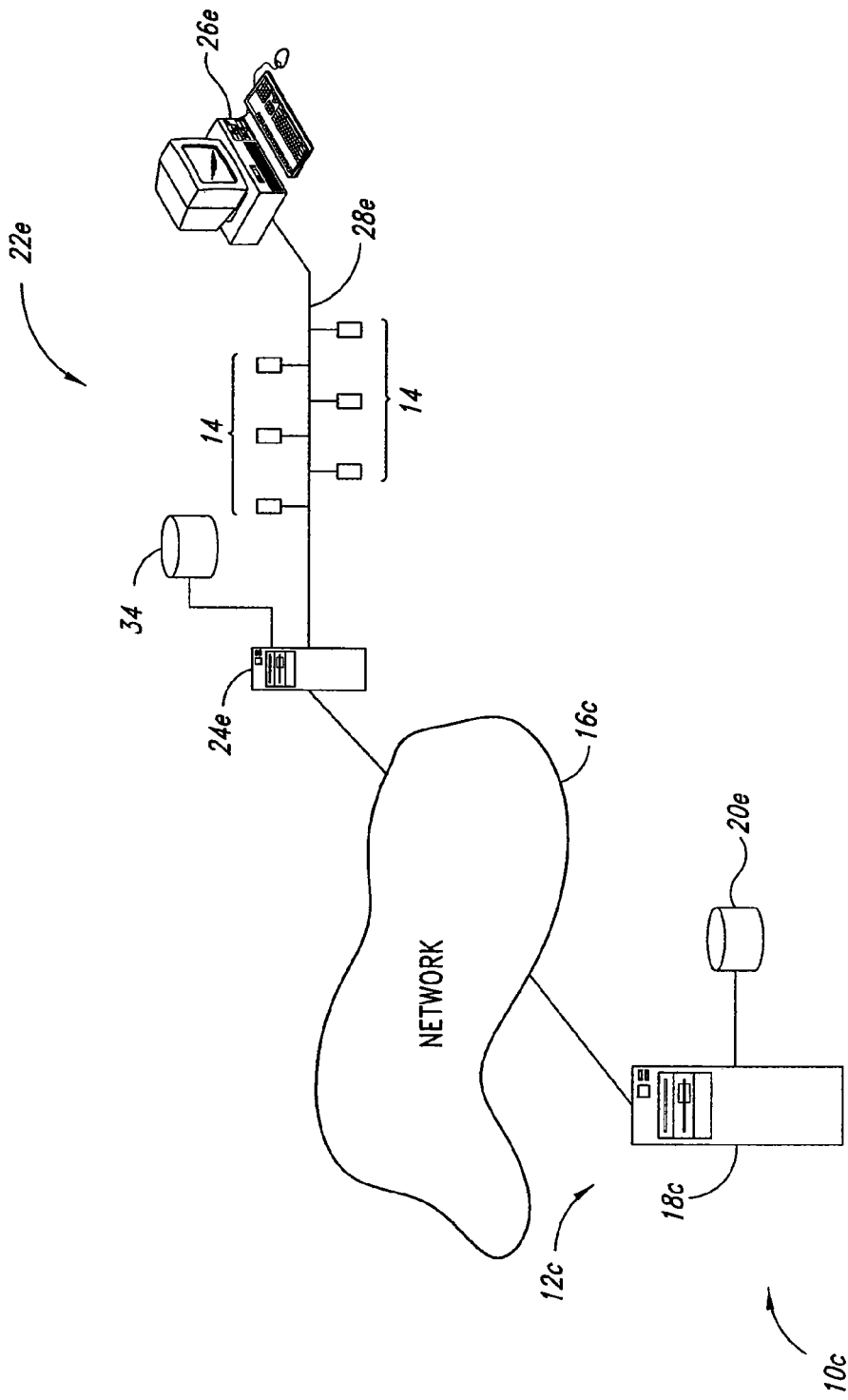
FIG. 3 is a schematic diagram of an object evaluation system including a host system and a test system remotely located from the host system and associated with a financial entity including a respective database, according to another illustrated embodiment.

FIG. 3 shows an object evaluation system 10c according to another illustrated embodiment.

The object evaluation system 10c includes one or more test device systems 22e. The test device system 22e includes one or more computing systems such as server computing system 24e and personal computing system 26e. The test device system 22e also includes a number of test devices 14 communicatively coupled via a network 28e. The network 28e may take a variety of forms including LANs, WANs, WLANs, WWANs, PSTN, to name a few. The test device system 22e further includes a proprietary storage or database 34. The proprietary storage or database 34 may contain executable modules and/or data. For example, the storage or database 34 may contain proprietary reference data that is specific to a financial entity which owns, operates, leases or controls the test device system 22e.

The object evaluation system 10c also includes host system 12c comprising one or more computing systems 18c and storage or databases 20e. The host system 12c is communicatively coupled to a test device system 24e via a network 16c.

Figure 4:
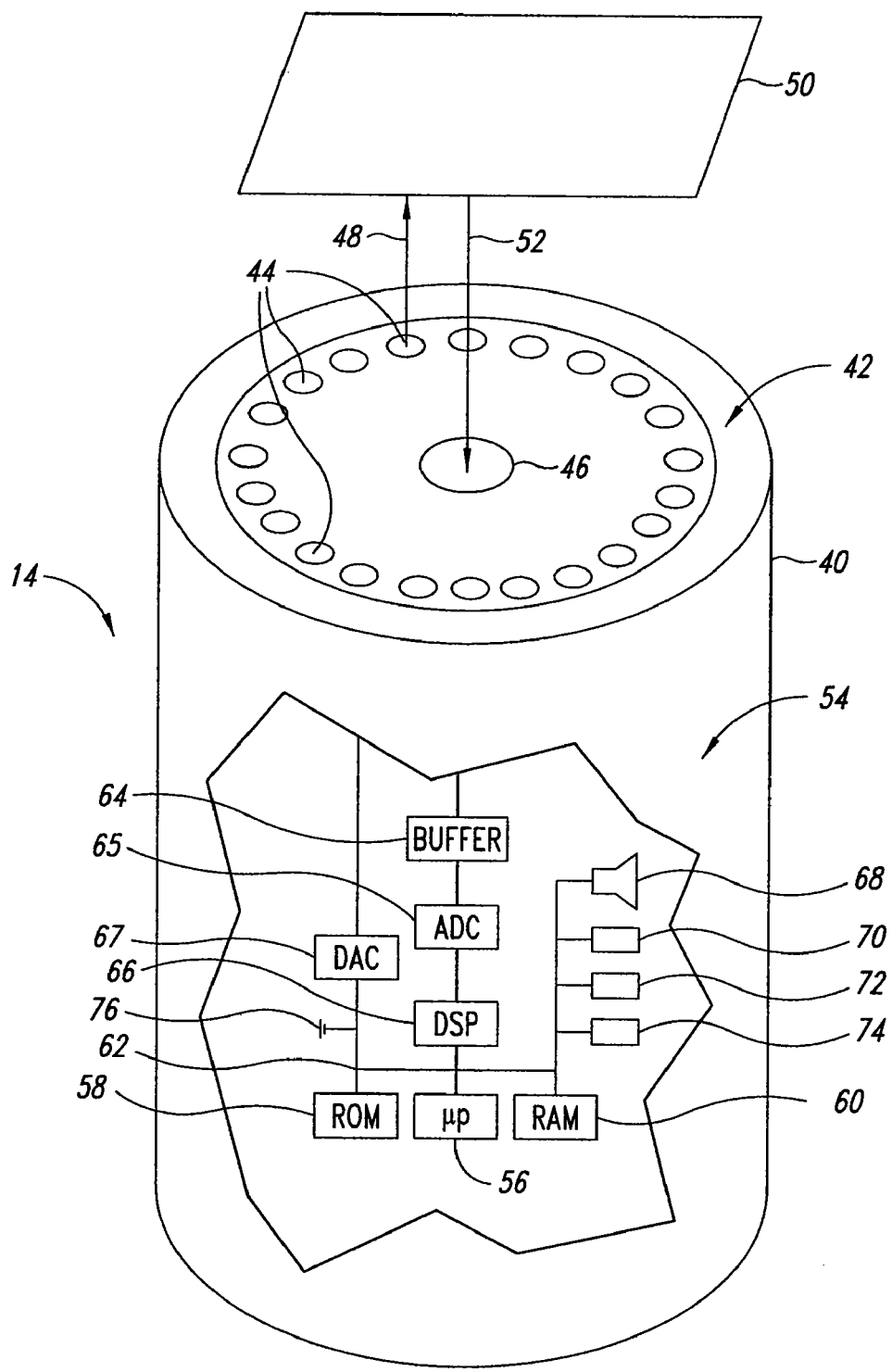
FIG. 4 is a partially cutaway isometric view of a test device illuminating an object, according to one illustrated embodiment.

FIG. 4 shows a test device 14 according to one illustrated embodiment.

The test device 14 may include a housing 40 with an opening or window 42 proximateone end thereof. The test device 14 may include one or more sources 44 (only three called out in FIG. 4) operable to emit electromagnetic energy. While a plurality of sources 44 are illustrated, some embodiments may employ a single source 44. The test device 14 may also include one or more sensors 46 configured and positioned to receive electromagnetic energy returned 52 from the object 50.

The sources 44 may take a variety of forms which are operable to emit electromagnetic energy. The sources 44 may, for example, take the form of one or more light emitting diodes (LEDs). Alternatively, or additionally, the sources 44 may take the form of one or more lasers, for example one or more laser diodes. The lasers may, or may not, be tunable lasers. Alternatively, or additionally, the sources 44 may take the form of one or more incandescent sources such as conventional or halogen light bulbs. Alternatively, or additionally, the sources 44 may take the form of one or more organic LEDs (OLEDs, also referred to in the relevant art as "electronic paper"), which may advantageously be formed on a flexible substrate.

One, more or all of the sources 44 may be operable to emit in part or all of an "optical" portion of the electromagnetic spectrum, including the (human) visible portion, near infrared portion and/or or near ultraviolet portions of the electromagnetic spectrum. Additionally, or alternatively, the sources 44 may be operable to emit electromagnetic energy other portions of the electromagnetic spectrum, for example the infrared, ultraviolet and/or microwave portions.

In some embodiments, at least some of the sources 44 are operable to emit in or at a different band than other of the sources 44. For example, one or more sources 44 may emit in a band centered around 450 nm, while one or more of the sources 44 may emit in a band centered around 500 nm, while a further source or sources emit in a band centered around 550 nm. In some embodiments, each source 44 emits in a band centered around a respective frequency or wavelength, different than each of the other sources 44. Using sources 44 with different band centers advantageously maximizes the number of distinct samples that may be captured from a fixed number of sources 44. This may be particularly advantageous where the test device 14 is relatively small, and has limited space or footprint for the sources 44.

The distribution of spectral content for each source 44 may vary as a function of drive level (e.g., current, voltage, duty cycle), temperature, and other environmental factors, depending on the specific source 44. Such variation may be advantageously actively employed to operate one or more of the physical sources 44 as a plurality of "logical sources," each of the logical sources operable to provide a respective emission spectra from a respective physical source 44. Thus, for example, the center of the band of emission for each source 44 may vary according to a drive level and/or temperature. For example, the center of the band of emission for LEDs will vary with drive current or temperature. One way the spectral content can vary is that the peak wavelength can shift. However, the width of the band, the skew of the distribution, the kurtosis, etc., can also vary. Such variations may be also be advantageously employed to operate the physical sources 44 as a plurality of logical sources. Thus, even if the peak wavelength were to remain constant, the changes in bandwidth, skew, kurtosis, and any other change in the spectrum can provide useful variations in the operation of the test device 14. Likewise, the center of the band of emission may be varied for tunable lasers. Varying the center of emission bands for one or more sources 44 advantageously maximizes the number of samples that may be captured from a fixed number of sources 44. Again, this may be particularly advantageous where the test device 14 is relatively small, and has limited space or footprint for the sources 44.

A field of emission of one or more sources 44 may be movable with respect to the housing 40. For example, one or more sources 44 may be movable mounted with respect to the housing 40, such as mounted for translation along one or more axes, and/or mounted for rotation or oscillation about one or more axes. Alternatively, or additionally, the test device 14 may include one or more elements operable to deflect or otherwise position the emitted electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, for example permanent magnets or electromagnets such as those associated with cathode ray tubes and/or mass spectrometers.

The sensor 46 can take a variety of forms suitable for sensing or responding to electromagnetic energy. For example, the sensor 46 may take the form of one or more photodiodes (e.g., germanium photodiodes, silicon photodiodes). Alternatively, or additionally, the sensor 46 may take the form of one or more photomultiplier tubes. Alternatively, or additionally, the sensor 46 may take the form of one or more CMOS image sensors. Alternatively, or additionally, the sensor 46 may take the form of one or more charge coupled devices (CCDs). Alternatively, or additionally the sensor 46 may take the form of one or more micro-channel plates. Other forms of electromagnetic sensors may be employed, which are suitable to detect the wavelengths expected to be returned in response to the particular illumination and properties of the object being illuminated.

The sensor 46 may be formed as individual elements, one-dimensional array of elements and/or two-dimensional array of elements. For example, the sensor 46 may be formed by one germanium photodiode and one silicon photodiode, each having differing spectral sensitivities. The test device 14 may employ a number of photodiodes with identical spectral sensitivities, with different colored filters (e.g., gel filters, dichroic filters, thin-film filters, etc) over the photodiodes to change their spectral sensitivity. This may provide a simple, low-cost approach for creating a set of sensors with different spectral sensitivities, particularly since germanium photodiodes are currently significantly more expensive that silicon photodiodes. Also for example, the sensor 46 may be formed from one CCD array (one-dimensional or two-dimensional) and one or more photodiodes (e.g., germanium photodiodes and/or silicon photodiodes). For example, the sensor 46 may be formed as a one- or two-dimensional array of photodiodes. A two-dimensional array of photodiodes enables very fast capture rate (i.e., camera speed) and may be particularly suited to use in assembly lines or high speed sorting operations. For example, the sensor 46 may be formed as a one- or two-dimensional array of photomultipliers. Combinations of the above elements may also be employed.

In some embodiments, the sensor 46 may be a broadband sensor sensitive or responsive over a broad band of wavelengths of electromagnetic energy. In some embodiments, the sensor 46 may be a narrowband sensor sensitive or responsive over a narrow band of wavelengths of electromagnetic energy. In some embodiments, the sensor 46 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

A field of view of the sensor 46 or one or more elements of the sensor 46 may be movable with respect to the housing 40. For example, one or more elements of the sensor 46 may be movable mounted with respect to the housing 40, such as mounted for translation along one or more axes, and/or mounted for rotation or oscillation about one or more axes. Alternatively, or additionally, the test device 14 may include one or more elements operable to deflect or otherwise position the returned electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers.

In some embodiments, the source 44 may also serve as the sensor 46. For example, an LED may be operated to emit electromagnetic energy at one time, and detect returned electromagnetic energy at another time. For example, the LED may be switched from operating as a source to operating as a detector by reverse biasing the LED. Also for example, an LED may be operated to emit electromagnetic energy at one time, and detect returned electromagnetic energy at the same time.

The test device 14 includes a control subsystem 54. The control subsystem 54 may include a microprocessor 56 and computer-readable media, for example one or more memories such as read only memory (ROM) 58 and random access memory (RAM) 60. One or more buses may couple the ROM 58 and RAM 60 to the microprocessor 56. The buses 62 may take a variety of forms including an instruction bus, data bus, other communications bus and/or power bus. The nonvolatile ROM 58 may store instructions and/or data for controlling the test device 14. The volatile RAM 60 may store instructions and/or data for use during operation of the test device 14.

The control subsystem 54 may optionally include a buffer 64 to buffer information received from the sensor 46. The control subsystem 54 may further optionally include a digital signal processor (DSP) 66 processor coupled to process information received from the sensor 46 via the buffer 64. The control subsystem 54 may further optionally include an analog to digital converter (ADC) 65 and/or digital to analog converter (DAC) 67. An ADC 65 may, for example, be used for converting analog photodiode responses into digital data for further analysis and/or transmission. A DAC 67 may, for example, be used for converting digital computer commands into analog LED current levels. The control subsystem 54 may additionally or alternatively optionally include an analog signal processor, which may be particularly useful where the sensor takes the form of one or more photodiodes.

The control subsystem 54 may include a user interface including one or more user interface devices. For example, the control subsystem 54 may include one or more speakers or microphones 68. Also for example, the control subsystem 54 may include and/or one or more visual indicators 70, such as one or more LEDs, liquid crystal displays (LCD), or other visual indicator. The LCD may, for example, take the form of a touch sensitive LCD, which displays a graphical user interface, operable by the user of the test device 14. Additionally, or alternatively, the control subsystem 54 may include one or more user operable input elements 74, such as switches or keys. The input elements 74 may include a switch for turning the test device ON and OFF. Additionally, or alternatively, the input elements 74 may include one or more switches or keys for controlling the operation of the test device 14, for example, downloading or uploading data or instructions to, or from the test device.

The control subsystem 54 may further include one more communication ports 72, for example, a USB port, infrared transceiver, or RF transceiver. Such may allow the transmission of data, instructions and/or results, to or from the test device 14.

The test device 14 may also include a power source 76. The power source may take the form of a portable power source, for example one or more batteries, fuel cells, and/or super- or ultra-capacitors. Additionally, or alternatively, the power source 76 may take the form of a fixed power source, such as a cable plugged into a port of a computer or a conventional electrical receptacle (e.g., wall outlet).

The microprocessor 56 employs instructions and or data from the ROM 58 and RAM 60 in controlling operation of the test device 14. For example, the microprocessor 56 operates the sources 44 in one or more sequences. The sequences determine an order in which the sources 44 are turned On and Off. The sequences may also indicate an ordered pattern of drive levels (e.g., current levels, voltage levels, duty cycles) for the sources 44. Thus, for example, a microprocessor 56 may cause the application of different drive levels to respective ones of the sources 44 to cause the sources 44 to emit in distinct bands of the electromagnetic spectrum. The DSP 66 and/or microprocessor 56 may process information generated by the sensor 46, which is indicative of the response by at least a portion of the object 50 to illumination by the sources 44. The information at any given time may be indicative of the response by the object 50 to illumination by one or more of the sources 44. Thus, the information over a period of time may be indicative of the responses by the object 50 to sequential illumination by each of a plurality of the sources 44, where each of the emission spectra of each of the sources 44 has a different center, bandwidth and/or other more complex differences in spectral content, such as those described above (e.g., width of the band, the skew of the distribution, the kurtosis, etc.).

Computing Systems

Figure 5:
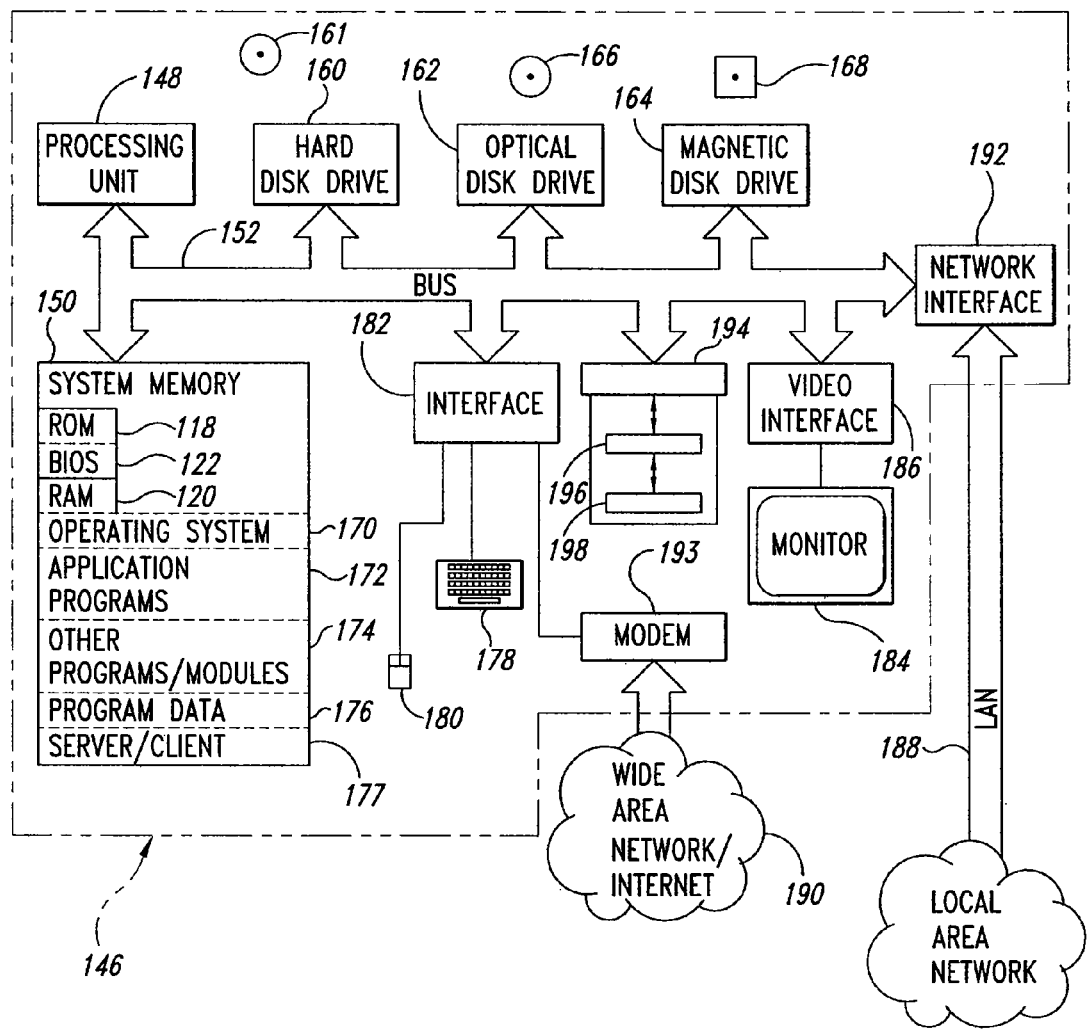
FIG. 5 is a functional block diagram of a computing system suitable for use as the host system of FIGS. 1-3 or other computing system, according to one illustrated embodiment.

FIG. 5 shows a conventional personal computer referred to herein as computing system 146 that may be appropriately configured to function as either the computing system 18 of the host system 12 (FIG. 1-3), the personal computing system 26 of the test device system 22, and/or conventional computing system 32.

The computing system 146 includes a processing unit 148, a system memory 150 and a system bus 152 that couples various system components including the system memory 150 to the processing unit 148. The processing unit 148 may be any logical processing unit, such as one or more central processing units (CPUs), digital signal processors (DSPs), application-specific integrated circuits (ASICs), field programmable gate arrays (FPGAs), etc. Unless described otherwise, the construction and operation of the various blocks shown in FIG. 5 are of conventional design. As a result, such blocks need not be described in further detail herein, as they will be understood by those skilled in the relevant art.

The system bus 152 can employ any known bus structures or architectures, including a memory bus with memory controller, a peripheral bus, and/or a local bus. The system memory 150 includes ROM 154 and RAM 156. A basic input/output system ("BIOS") 158, which can form part of the ROM 154, contains basic routines that help transfer information between elements within the computing system 146, such as during startup.

The computing system 146 also includes one or more spinning media memories such as a hard disk drive 160 for reading from and writing to a hard disk 161, and an optical disk drive 162 and a magnetic disk drive 164 for reading from and writing to removable optical disks 166 and magnetic disks 168, respectively. The optical disk 166 can be a CD-ROM, while the magnetic disk 168 can be a magnetic floppy disk or diskette. The hard disk drive 160, optical disk drive 162 and magnetic disk drive 164 communicate with the processing unit 148 via the bus 152. The hard disk drive 160, optical disk drive 162 and magnetic disk drive 164 may include interfaces or controllers coupled between such drives and the bus 152, as is known by those skilled in the relevant art, for example via an IDE (i.e., Integrated Drive Electronics) interface. The drives 160, 162 and 164, and their associated computer-readable media 161, 166 and 168, provide nonvolatile storage of computer-readable instructions, data structures, program modules and other data for the computing system 146. Although the depicted computing system 146 employs hard disk 161, optical disk 166 and magnetic disk 168, those skilled in the relevant art will appreciate that other types of spinning media memory computer-readable media may be employed, such as digital video disks ("DVDs"), Bernoulli cartridges, etc. Those skilled in the relevant art will also appreciate that other types of computer-readable media that can store data accessible by a computer may be employed, for example, non-spinning media memories such as magnetic cassettes, flash memory cards, RAMs, ROMs, smart cards, etc.

Program modules can be stored in the system memory 150, such as an operating system 170, one or more application programs 172, other programs or modules 174, and program data 176. The applications programs 172 may include one or more programs for: locating test devices 14, downloading instructions such as executable modules to test devices 14, uploading responses to illumination from test devices 14, selecting appropriate test sequences, analyzing results of the test sequences, and delivering the analysis to the test devices 14. The system memory 150 also includes one or more communications programs 177 for permitting the computing system 146 to access and exchange data with sources such as websites of the Internet, corporate intranets, or other networks, as well as other server applications on server computers. The communications program 177 may take the form of one or more server programs. Alternatively, or additionally, the communications program may take the form of one or more browser programs. The communications program 177 may be markup language based, such as hypertext markup language ("HTML"), Extensible Markup Language (XML) or Wireless Markup Language (WML), and operate with markup languages that use syntactically delimited characters added to the data of a document to represent the structure of the document. A number of Web clients or browsers are commercially available such as NETSCAPE NAVIGATOR® from America Online, and INTERNET EXPLORER® available from Microsoft Corporation of Redmond Wash.

While shown in FIG. 5 as being stored in the system memory 150, the operating system 170, application programs 172, other program modules 174, program data 176 and communications program 177 can be stored on the hard disk 161 of the hard disk drive 160, the optical disk 166 of the optical disk drive 162 and/or the magnetic disk 168 of the magnetic disk drive 164.

A user can enter commands and information to the computing system 146 through input devices such as a keyboard 178 and a pointing device such as a mouse 180. Other input devices can include a microphone, joystick, game pad, scanner, button, key, microphone with voice recognition software, etc. These and other input devices are connected to the processing unit 148 through an interface 182 such as a serial port interface that couples to the bus 152, although other interfaces such as a parallel port, a game port or a universal serial bus ("USB") can be used. A monitor 184 or other display devices may be coupled to the bus 152 via video interface 186, such as a video adapter. The computing system 146 can include other output devices such as speakers, printers, etc.

The computing system 146 can operate in a networked environment 10 (FIGS. 1-3) using logical connections to one or more remote computers. The computing system 146 may employ any known means of communication, such as through a local area network ("LAN") 188 or a wide area network ("WAN") or the Internet 190. Such networking environments are well known in enterprise-wide computer networks, intranets, extranets, and the Internet.

When used in a LAN networking environment, the computing system 146 is connected to the LAN 188 through an adapter or network interface 192 (communicatively linked to the bus 152). When used in a WAN networking environment, the computing system 146 often includes a modem 193 or other device for establishing communications over the WAN/Internet 190. The modem 193 is shown in FIG. 5 as communicatively linked between the interface 182 and the WAN/Internet 190. In a networked environment, program modules, application programs, or data, or portions thereof, can be stored in a server computer (not shown). Those skilled in the relevant art will readily recognize that the network connections shown in FIG. 5 are only some examples of establishing communications links between computers, and other communications links may be used, including wireless links.

The computing system 146 may include one or more interfaces such as slot 194 to allow the addition of devices 196, 198 either internally or externally to the computing system 146. For example, suitable interfaces may include ISA (i.e., Industry Standard Architecture), IDE, PCI (i.e., Personal Computer Interface) and/or AGP (i.e., Advance Graphics Processor) slot connectors for option cards, serial and/or parallel ports, USB ports (i.e., Universal Serial Bus), audio input/output (i.e., I/O) and MIDI/joystick connectors, and/or slots for memory.

The term "computer-readable medium" as used herein refers to any medium that participates in providing instructions to processing unit 148 for execution. Such a medium may take many forms, including but not limited to, non-volatile media, volatile media, and transmission media. Non-volatile media includes, for example, hard, optical or magnetic disks 161, 166, 168, respectively. Volatile media includes dynamic memory, such as system memory 150. Transmission media includes coaxial cables, copper wire and fiber optics, including the wires that comprise system bus 152. Transmission media can also take the form of acoustic or light waves, such as those generated during radio wave and infrared data communications.

Common forms of computer-readable media include, for example, floppy disk, flexible disk, hard disk, magnetic tape, or any other magnetic medium, CD-ROM, any other optical medium, punch cards, paper tape, any other physical medium with patterns of holes, RAM, PROM, EPROM, EEPROM, FLASH memory, any other memory chip or cartridge, a carrier wave as described herein, or any other medium from which a computer can read.

Various forms of computer readable media may be involved in carrying one or more sequences of one or more instructions to processing unit 148 for execution. For example, the instructions may initially be carried on a magnetic disk of a remote computer. The remote computer can load the instructions into its dynamic memory and send the instructions over a telephone line using a modem. A modem 193 local to computer system 146 can receive the data on the telephone line and use an infrared transmitter to convert the data to an infrared signal. An infrared detector coupled to the system bus 152 can receive the data carried in the infrared signal and place the data on system bus 152. The system bus 152 carries the data to system memory 150, from which processing unit 148 retrieves and executes the instructions. The instructions received by system memory 150 may optionally be stored on a storage device either before or after execution by processing unit 148.

Figure 6:
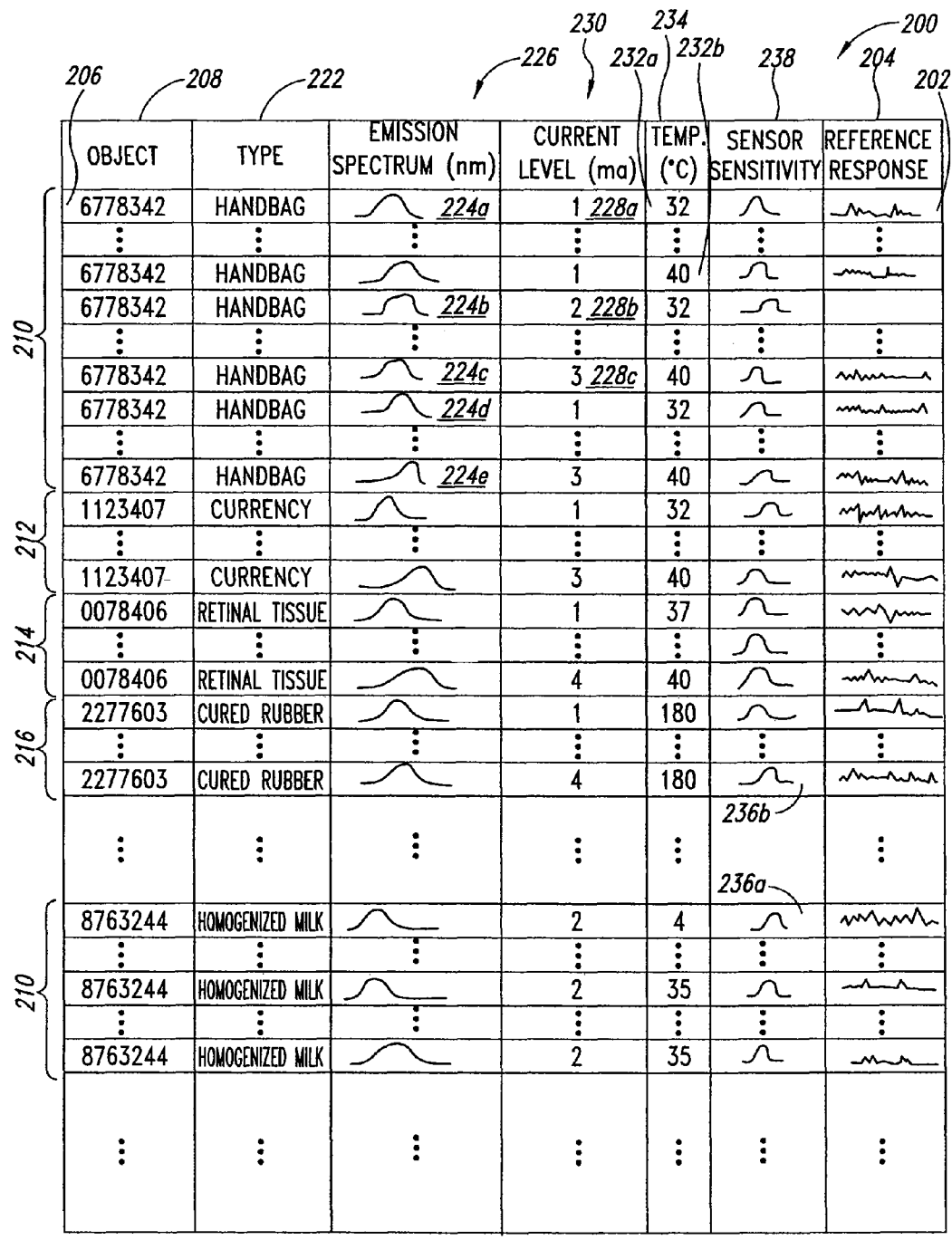
FIG. 6 is a schematic diagram of a data structure of reference data stored in a computer-readable memory, according to one illustrated embodiment.

FIG. 6 shows a data structure 200 which may be stored in one of the storage media or databases 161, 166, 168 (FIG. 5), 20, 34 (FIGS. 1-3), 58, 60 (FIG. 4), according to one illustrated embodiment.

The data structure 200 stores reference responses 202 (only one called out, illustrated in column 204) for various objects 50 (FIG. 4) identified by object identifiers 206 (only one called out, illustrated in column 208).

The data structure 200 may store a reference response 202 for a variety of objects 50, for example a specific handbag or type of handbag 210. The data structure 200 may store reference responses for media, for example: identification documents such as passports, identity cards (e.g., national, state, provincial, military, employer, school, organization), driver's licenses, and/or birth or naturalization certificates; financial documents such as currency 212, checks, bonds, and/or securities; and/or legal documents such as licenses, permits, assignments, deeds, wills, declarations, oaths, agreements, pleadings, or motions. The data structure 200 may also store reference responses 202 for tissue 214, for example, reference responses that identify (e.g., unique individual) or characterize (e.g., normal, abnormal) bodily tissue such as retinal tissue or blood. The data structure 200 may additionally, or alternatively, store data corresponding to a manufacturing process, such as reference responses for various processing steps for curing rubber 216. The data structure 200 may additionally, or alternatively, store data related to quality control, for example, reference responses for properly homogenized milk 218.

The data structure 200 may include an object type identifier 220 (only one called out in FIG. 6, illustrated in column 222). The object type identifier may provide a general and/or specific description of the type of object (e.g., handbag, currency, U.S. Ten Dollar Note, retinal tissue, semiconductor circuit masking operation, etc.). Additionally, or alternatively, the object type identifier 220 may provide broad and/or specific description of the physical characteristics of the object type (e.g., paper, MYLAR®, canvas, A4, serial number, leather, green, 36° C., 5 foot and 11 inches, 160 pounds, brown hair, etc.).

For each object 50, the data structure 200 may store reference responses 202 corresponding to respective physical and or logical sources 44 (FIG. 4) or the respective emission spectra for sources 44. For example, the data structure 200 stores reference responses 202 for a number of sources 44 or respective emission spectra 224a-224e (collectively 224) for the handbag 210. The emission spectra 224 may be represented in a variety of ways, for example as one-dimensional or multi-dimensional functions or waveforms or as individual values indicative of one or more characteristics, for example peak wavelength or primary band.

The data structure 200 may store reference responses 202 at a variety of drive levels for each of the sources 44. For example, the data structure 200 may store reference responses 202 at current levels 228a-228c (only three called out in FIG. 6, collectively 228, illustrated in column 230). While the reference responses 202 are illustrated as one-dimensional functions or waveforms, the reference responses may take any of a variety of forms. For example, in some embodiments each of the reference responses 202 with take the form of a single value or number for a given object, source, drive-level and/or temperature combination. In other embodiments, each of the reference responses 202 may take the form of a multi-dimensional function or waveform (e.g., two, three or greater dimensions). Such may be suitable where, for example, the sensor 46 takes the form of a CCD array, rather than a photodiode.

Additionally, the data structure 200 may include reference responses 202 where the source 44 and/or sensor 46 is at a variety of temperatures 232a, 232b (only two called out in FIG. 6, illustrated in column 234). This allows for variance in emission spectra and/or reception to be accounted for in the data structure 200. Thus, identification of a source 44, a driving level 228 and/or a temperature may allow selection of an appropriate reference response 202 for use in analyzing test data measured or determined by the test device 14, as further explained below.

Additionally, or alternatively, the data structure 200 may include reference responses 202 for a variety of sensor sensitivities 236a, 236b (only two called out in FIG. 6, illustrated in column 238). This allows for variance in sensitivity of various sensors 46 to be accounted for in the data structure 200. Thus, identification of a sensor 46 may allow selection of an appropriate reference response 202 for use in analyzing test data measured or determined by the test device 14, as further explained below.

The data structure 200 may additionally include location or position information that identifies a location or position on the reference object from which the reference response was taken and/or the positions of the sources(s) 44 and/or sensor (s) 46 relative to the reference object. Reference responses from multiple locations on a reference object may be stored in the data structure 200. Varying the location of testing or sampling may further contribute to the inherent encryption associated with varying the sequence.

FIGS. 7-28 show methods of operating the computing system 18 (FIGS. 1-3) of the host system 12 and/or test device 14, according to various embodiments. The Figures generally illustrate operations of the computing system 18 or host system 12 in a column on the left side of the Figure, while operations of the test device 14 are generally illustrated in a column on the right side of the Figure. The flow of operation is generally illustrated by vertically extending arrows. The flow of data between the computing system 18 or host system 12 and the test device 14 is generally illustrated by arrows extending between the right and left columns of FIGS. 7-9, 15, 16, 24, 25A and 25B. Some Figures use a center column to illustrate operations that may be performed by either the computing system 18 or test device 14.

Figure 7:
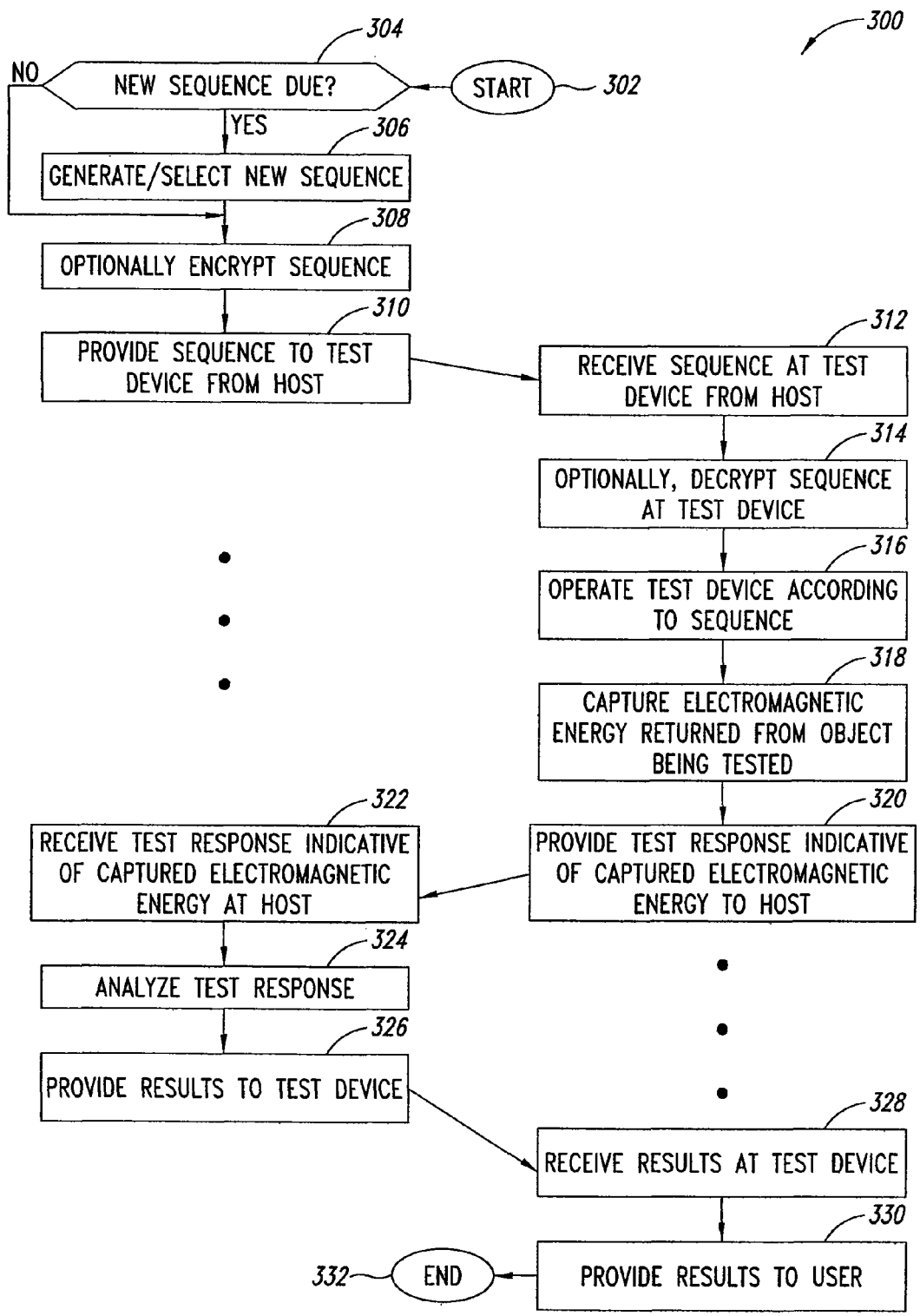
FIG. 7 is a flow diagram showing a method of operating a host system and a test device remotely located with respect to the host system, the method employing both inherent and conventional encryption techniques to operate in a secure manner, according to one illustrated embodiment.

FIG. 7 shows a method 300 of operating the computing system 18 (FIGS. 1-3) of the host system 12 and test device 14 in a secure manner, according to one illustrated embodiment.

The method 300 may start at 302. For example, the method 300 may start in response to activation of the computing system 18, or in response to a user input, or a signal from a sensor.

At 304, the computing system 18 determines whether a new sequence is due. As discussed above, the sequence defines an order of activation for the sources 44, and may optionally define a sequence of drive levels and/or temperature levels for one or more of the sources 44 within the sequence. In some embodiments, the sequence can be varied periodically. In other embodiments, the sequence may be varied randomly. In further embodiments, the sequence may be varied with each iteration. In still other embodiments, the sequence may be varied based on a time and/or date.

At 306, the computing system 18 generates or selects a new sequence. The computing system 18 may generate the new sequence using a random number generator (RNG). Alternatively, the computing system 18 may select a new sequence from a set of sequences stored in the memory or database 20. Alternatively, the computing system 18 may generate a new sequence based on a current time and/or date. Additionally or alternatively, the computing system 18 may generate a new sequence based on a combination of environmental conditions (e.g., date and time, temperature, GPS location, etc.) and stored data (e.g., constants, functions for generating sequences from simple inputs, etc.).

At 308, the computing system 18 optionally conventionally encrypts the sequence. At 310, the computing system 18 provides the sequence to the test device 14.

At 312, the test device 14 receives the sequence from the computing system 18. Optionally, at 314, the test device 14 conventionally decrypts the sequence. At 316, the test device 14 operates according to the sequence. For example, the control subsystem 54 or microprocessor 56 may activate or turn ON selected ones or groups of the sources 44, in the order of the defined sequence. Also, for example, the control subsystem 54 or microprocessor 56 may apply a drive level such as a current, voltage or duty cycle to the sources 44 and/or change temperature of the sources 44 (e.g., via a heater or thermoelectric cooler) according to the sequence.

At 318, the sensor 46 captures electromagnetic energy returned from the object 50 being subject to the test. Returned electromagnetic energy may take the form of electromagnetic energy reflected, fluoresced, or otherwise returned from the object 50. The returned electromagnetic energy is the response by the object 50 to the particular illumination during the relevant period. At 320, the test device 14 provides a signal indicative of the response or captured electromagnetic energy to the computing system 18.

At 322, the computing system 18 receives the signal indicative of the response or captured electromagnetic energy. At 324, the computing system 18 analyzes the received captured electromagnetic energy. At 326, the computing system 18 provides results to test device 14.

At 328, the test device 14 receives the results. At 330, the test device 14 provides results to the end user, for example, via one or more elements 68, 70 of the user interface. The method 300 may terminate at 332. In some embodiments, the method 300 would return control back to 304 in lieu of terminating at 332. In other embodiments, the method 300 may operate as separate processes or threads, in parallel or concurrently with one another.

Varying the sequence produces an inherent encryption of the signals indicative of the test responses and/or the results. The variation makes it difficult for someone to determine or fake test responses for a given object since the test response varies based on the particular illumination sequence employed. Additionally, the differences in sources 44 (e.g., LED composition), between test devices 14, creates a unique signature for responses taken from each test device 14. A knowledge of this unique signature may be used in calibration for decoding the test response provided by the specific test device 14, so it can also be considered an inherent form of encryption. Inherent encryption may be particularly advantageous where security is a concern, for example where identity documents are being authenticated, where financial instruments are being authenticated or where goods are being authenticated to detect forgeries. Thus, the sequence may be varied randomly, periodically, based on time and/or date, or on demand. This inherent variation may be bolstered by more conventional encryption, for example public/private key encryption, for example RSA encryption. Thus, the test response may be encrypted using conventional encryption techniques. Additionally, or alternatively, the sequence may be encrypted using conventional encryption techniques. Additionally, or alternatively, if the sequence is transmitted, it may be transmitted separately from the test results, reducing the likelihood of interception of both. It should be noted that even if both the sequence and resulting test response were intercepted, such information would have limited value since the sequence would or could soon be changed.

Figure 8:
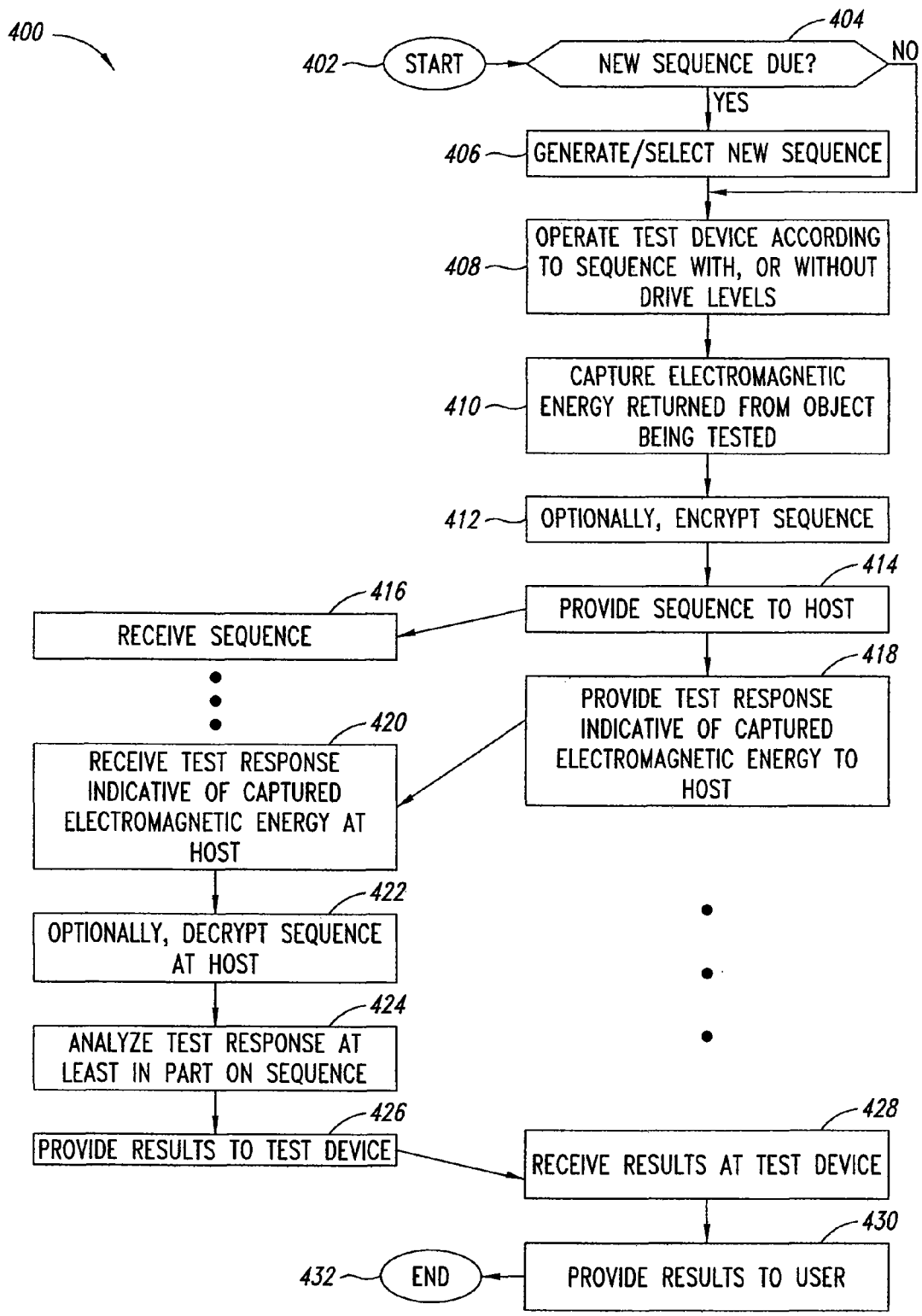
FIG. 8 is a flow diagram showing a method of operating a host system and a test device remotely located with respect to the host system, the method employing both inherent and conventional encryption techniques to operate in a secure manner, according to another illustrated embodiment.

FIG. 8 shows a method 400 of operating the computing system 18 and test device 14 in a secure manner, according to another illustrated embodiment.

The method 400 starts at 402. For example, the method 400 may start in response to the activation or powering of the test device 14, or in response to a user input or signal from a sensor.

At 404, the test device 14 determines whether a new sequence is due. If a new sequence is due, the test device 14 generates or selects a new sequence at 406. The test device 14 may generate a sequence using a random number generator (RNG). Alternatively, the test device 14 may select a new sequence from a set of sequences stored in a memory (e.g., ROM 58, RAM 60) of the test device 14. Alternatively, the test device 14 may generate a new sequence based on a current time and/or date.

At 408, the test device 14 operates according to the sequence with, or without, varying drive levels of the sources 44. As noted above, the drive levels may take a variety of forms, for example, current or voltage levels, or duty cycles.

At 410, the sensor 46 captures electromagnetic energy returned from the object 50 being tested. As noted above, the returned electromagnetic energy is the response by the object 50 to the particular illumination during the period. Optionally, at 412, the test device 14 conventionally encrypts the sequence. At 414, the test device provides the sequence to the computing system 18.

At 418, the test device 14 provides a signal indicative of the response or captured electromagnetic energy to the computing system 18.

At 416, the computing system 18 receives the sequence. At 420, the computing system 18 receives the signal indicative of the captured electromagnetic energy. Optionally, at 422, the computing system 18 decrypts the sequence. At 424, the computing system 18 analyzes the received signal indicative of the response or captured electromagnetic energy, based at least in part on the received sequence. At 426, the computing system 18 provides results of the analysis to the test device 14.

At 428, the test device 14 receives the results. At 430, the test device 14 provides the results to an end user, for example, via one or more elements 68, 70 of the user interface. The method 400 may terminate at 432. In some embodiments, the method 400 may return control back to 404 in lieu of terminating at 432. In other embodiments, the method 400 may operate as separate processes or threads, in parallel or concurrently with one another.

Figure 9:
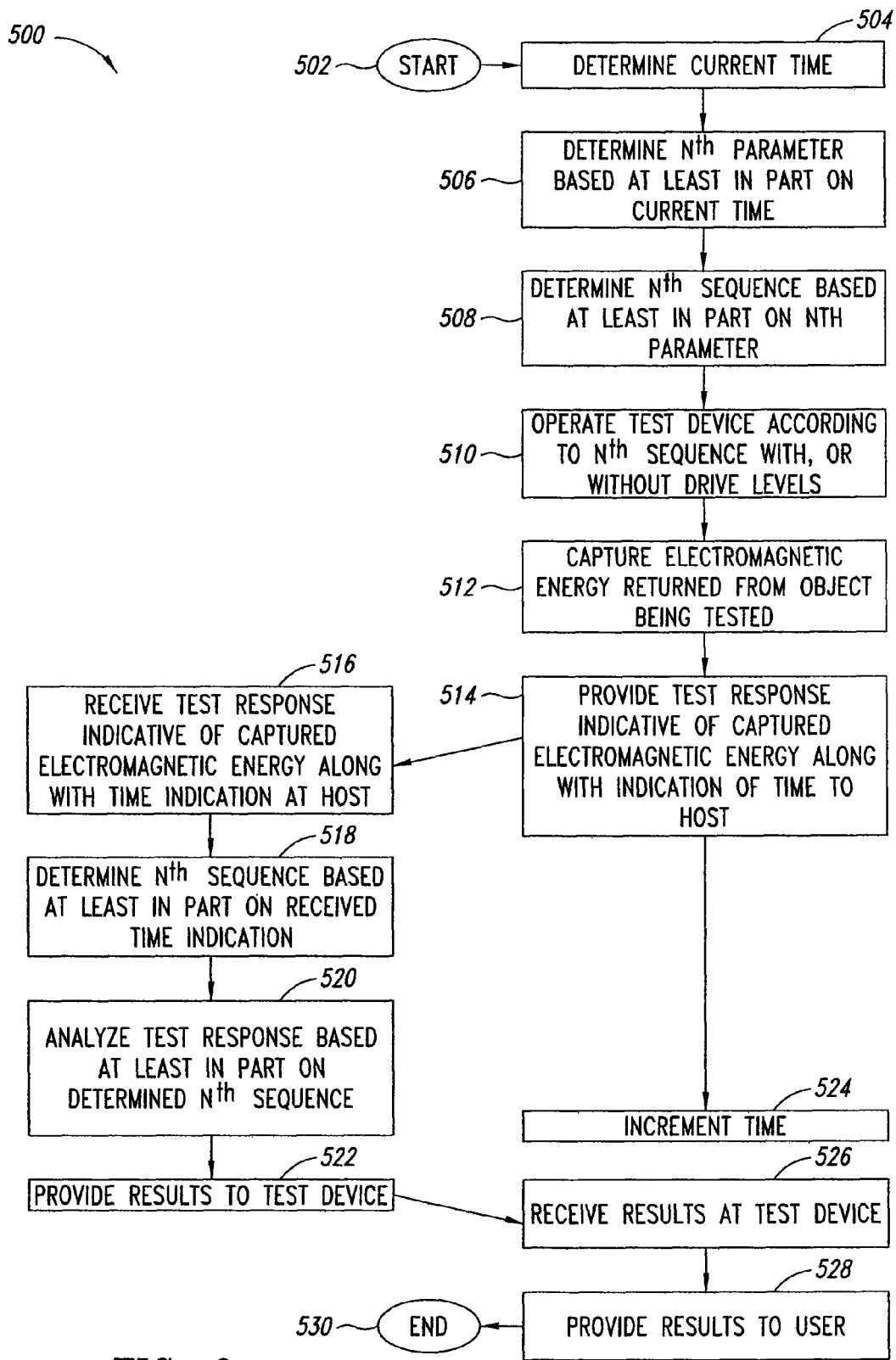
FIG. 9 is a flow diagram showing a method of operating a host system and test device remotely located with respect to the host system, the method employing both inherent and conventional encryption techniques to operate in a secure manner, according to a further illustrated embodiment.

FIG. 9 shows a method 500 of operating the computing system 18 of the host system 12 and test device 14 in a secure manner, according to yet another illustrated embodiment.

The method 500 starts at 502. For example, the method 500 may start in response to activation or powering of the test device 14, or in response to a user input, or a signal from a sensor.

At 504, the test device 14 determines a current time which may, or may not also reflect the current date. The test device 14 may rely on an internal clock that may or may not be global, and may be synchronized with a clock on the computing system 18. At 506, the test device 14 determines an $N^{th}$ parameter based, at least in part, on the current time. The modifier $N^{th}$ is employed because the parameter varies as the time varies. For example, a first parameter value is determined based on at first time, while a second, different parameter value is determined based on a second time.

At 508, the test device 14 determines an $N^{th}$ sequence based, at least in part, on the nth parameter. Thus, for example, the test device 14 determines a first sequence based on a first parameter, and at a later time determines a second sequence based on a second parameter.

At 510, the test device 14 operates according to the $N^{th}$ sequence, with, or without, varying drive levels of the sources 44. As noted above, the drive levels may take the form of current or voltage levels and/or duty cycles. At 512, the sensor 46 captures electromagnetic energy returned from the object 50 being tested or response to the particular illumination during a period. At 514, the test device 14 provides a signal indicative of the response or captured electromagnetic energy to the computing system 18 of the host system 12. The test device 14 may provide an indication of the time along with the signal indicative of the response. Alternatively, if the test device 14 operates quickly enough, the computing system 18 may employ the time of receipt or the time of transmission of the signal indicative of the response which is provided by the test device 14.

At 516, the computing system 18 receives the signal indicative of the response or captured electromagnetic energy. As noted above, the information received may include an indication of the time. At 518, the computing system 18 determines the $N^{th}$ sequence based, at least in part, on the time. The time may be determined from the indication received from the test device 14. At 520, the computing system 18 analyzes the signal indicative of the response or received captured electromagnetic energy, based at least in part on the determined $N^{th}$ sequence. At 522, the computing system 18 provides results to the test device 14.

At 524, the test device 14 increments the time. One of ordinary skill in the art will recognize that the test device 14 may increment the time at other positions in the flow of the method 500. At 526, the test device 14 receives the results. At 528, the test device 14 provides the results to an end user, for example, via one of the elements 68, 70 of the user interface. The method 500 may terminate at 530. In some embodiments, the method 500 would return control back to 504 in lieu of terminating at 530. In other embodiments, the method 500 may operate as separate processes or threads, in parallel or concurrently with one another.

Figure 10:
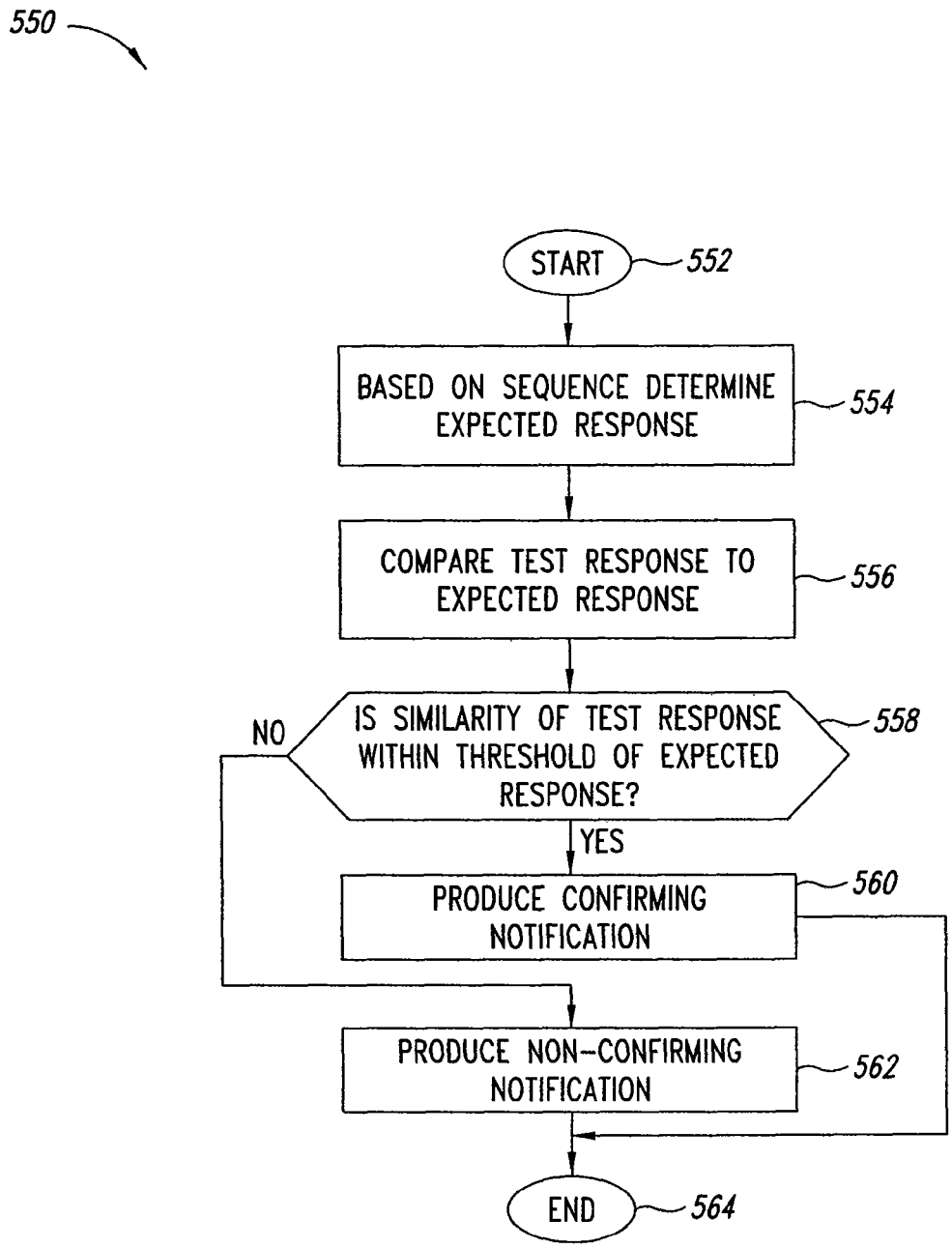
FIG. 10 is a flow diagram showing a method of operating the host system or test device remotely located with respect to the host system, to facilitate evaluation of an object, according to one illustrated embodiment.

FIG. 10 shows a method 550 of analyzing test responses, according to one illustrated embodiment. In some embodiments, the method 550 may be performed or executed by the computing system 18. In other embodiments, the method 550 may be performed or executed by test device 14.

The method 550 starts at 552. For example, the method 550 may start in response to a call within or from a software routine, program, or process. Alternatively, the method 550 may start in response to a user input or receipt of data or information.

At 554, an expected response is determined based on a sequence of illumination. As noted above, the sequence of illumination of the object 50 by the sources 44 may vary. Consequently, the response by the object 50 to the sequence of illumination will vary. Thus, for example, the object 50 may be sequentially illuminated with electromagnetic energy from a first band, then a second band, then a third band, etc. Alternatively, the object 50 may be sequentially illuminated with electromagnetic energy from a third band, then a second band, then a first band, etc. The response to the second sequence will likely be different from the response to the first sequence.

At 556, the received signal indicative of the response or captured electromagnetic energy is compared to the expected response. At 558, it is determined whether the response or captured electromagnetic energy is within a defined threshold of the expected response. If the response is within the defined threshold of the expected response, an appropriate confirming notification is produced at 560. The confirming notification may, or may not, include an indication of a level of confidence in the match. The confidence level may be represented in a variety of ways, for example as a percentage of discrepancies detected or how many standard deviations the match is from being an identical match. Alternatively, the confidence level may indicate the number of times a match with a threshold was found. For example, if a match was found in response to more than one sequence, at more than one location, and/or at more than one viewpoint or angle. If not, an appropriate non-confirming notification is produced at 562. The method may terminate at 564. In some embodiments, the method 550 may repeat. In other embodiments, the method 550 may operate as separate processes or threads, in parallel or concurrently with one another.

Figure 11:
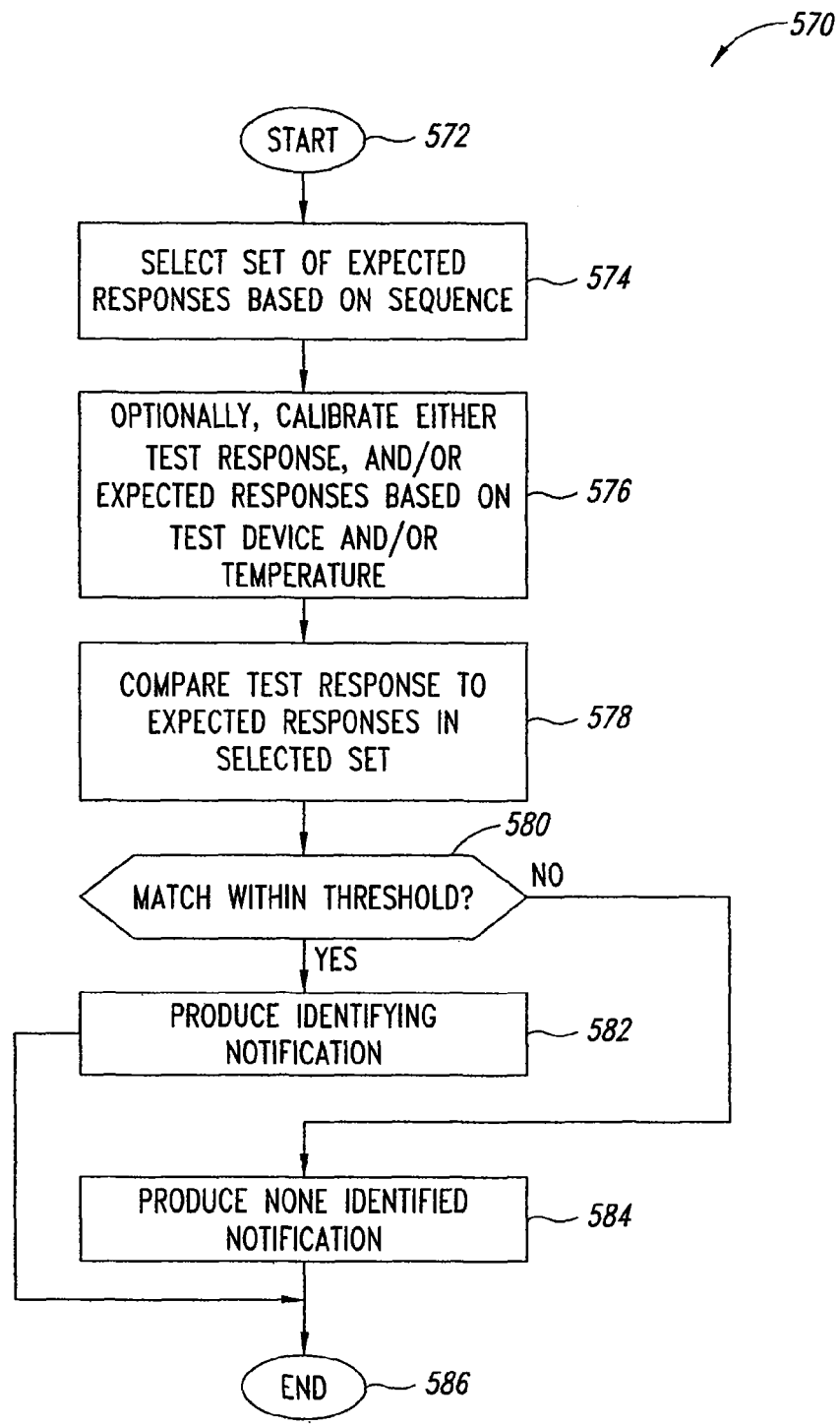
FIG. 11 is a flow diagram showing a method of operating the host system or test device remotely located with respect to the host system, to facilitate evaluation of an object, according to another illustrated embodiment.

FIG. 11 shows a method 570 of analyzing test responses, according to another illustrated embodiment. In some embodiments, the method 570 may be performed or executed by the computing system 18. In other embodiments, the method 570 may be performed or executed by test device 14.

The method 570 starts at 572. For example, the method 570 may start in response to a call from a program, routine, or process. Alternatively, the method 570 may start in response to a user input or receipt of data or information.

At 574, a set of expected responses are selected based on the sequence. For example, given a defined sequence, responses for one or more object (e.g., goods, documents, tissue) may be selected. The selection of the expected response may, or may not, be based on one or more temperatures at which the sources 44 or sensor 46 is operating or is expected to be operating.

Optionally, at 576, either the test response and/or the expected responses may be calibrated. The calibration may be based on a variety of factors or parameters. For example, the calibration may be based on a temperature at which the source 44 and/or sensor 46 is operating or expected to be operating. For example, where the sources 44 are LEDs, variations in emission spectra based on temperature may be accommodated. Also for example, the calibration may be based on the properties of specific sources 44. For example, where the sources 44 are LEDs variations in emission spectra based on manufacturing differences between specific sources 44 may be accommodated. For example, variations between different manufactures, different batches of sources 44 by the same manufacturer, or even between individual sources 44 in the same manufacturing batch may be accommodated.

At 578, the test response is compared to expected responses in the selected set. At 580, it is determined whether a match is within a suitable threshold. If the match is in a suitable threshold, an identifying notification is produced at 582. If the match is not within the threshold, an appropriate none-identified notification is produced at 584.

The method 570 may terminate at 586. In some embodiments, the method 570 would return control back to 574 in lieu of terminating at 586. For example, some embodiments may attempt to find matches for more than one sequence, at more than one location, and/or at more than one viewpoint or angle. In other embodiments, the method 570 may operate as separate processes or threads, in parallel or concurrently with one another.

Figure 12:
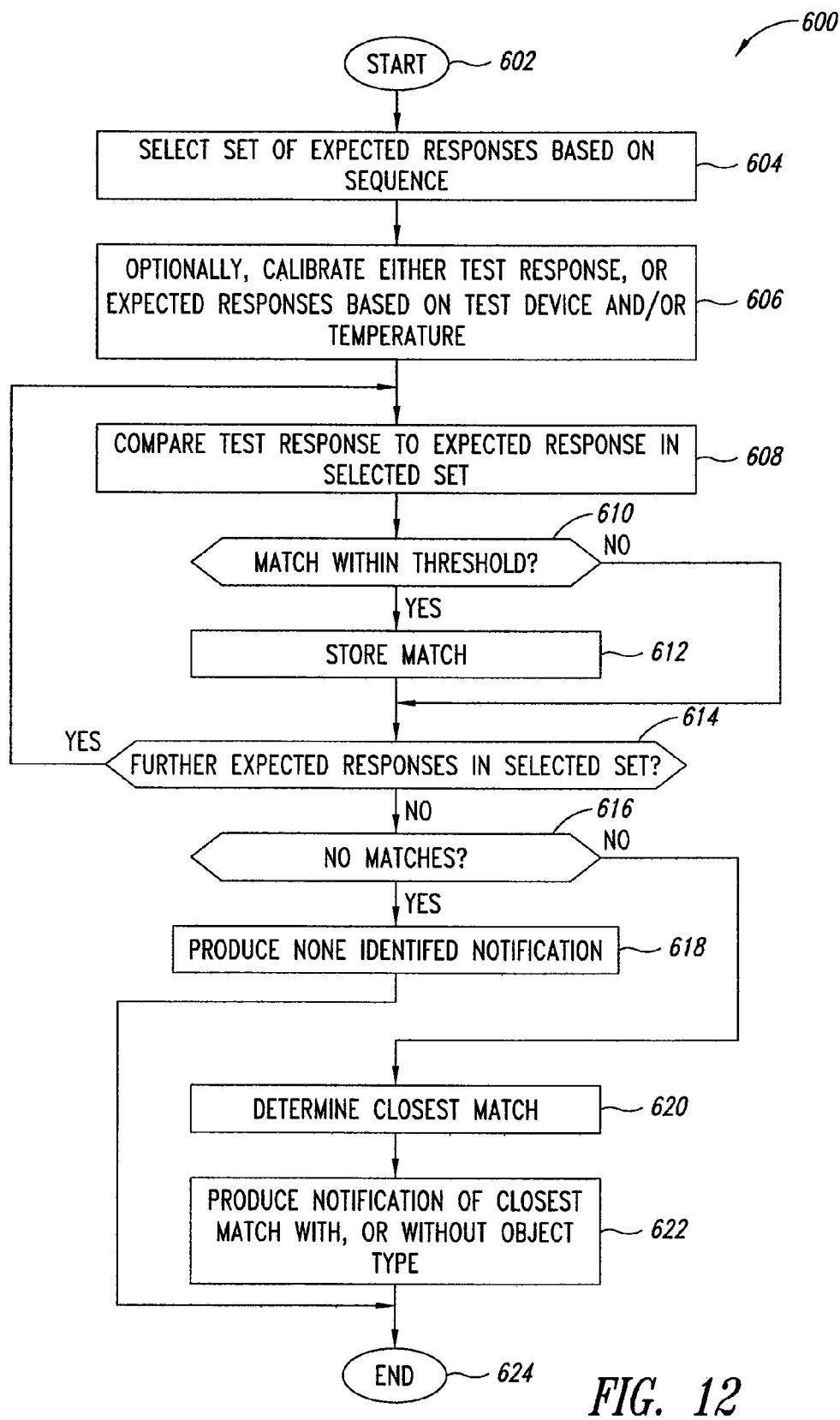
FIG. 12 is a flow diagram showing a method of operating the host or test device remotely located with respect to the host system, to facilitate evaluation, according to a further illustrated embodiment.

FIG. 12 shows a method 600 of analyzing test responses, according to a further illustrated embodiment. In some embodiments, the method 600 may be performed or executed by the computing system 18. In other embodiments, the method 600 may be performed or executed by test device 14.

The method 600 starts at 602. For example, the method 600 may start in response to a call from another program, routine, or process. Alternatively, the method 600 may start in response to a user input or receipt of data or information.

At 604, a set of expected responses is selected based on the sequence. Such was discussed above with reference to 574 of FIG. 11.

Optionally, at 606, the test response and/or expected responses may be calibrated. As discussed above in reference to 576 of FIG. 11, calibration may be based on a variety of factors or parameters.

At 608, the test response is compared to the expected response in a selected set, as discussed above in reference to 578 of FIG. 11. At 610, it is determined whether there is a match within a defined threshold, as discussed in reference to 580 of FIG. 11. If the match is within the defined threshold, the match is stored at 612 and control passes to 614. If the match is not within the defined threshold, control passes directly to 614.

At 614, it is determined whether there are further expected responses in the selected set. If there are further expected responses, control returns to 608. Otherwise, control passes to 616.

At 616, it is determined whether there are no matches. If there are no matches, a none identified notification is produced at 618, and the method 600 terminates at 624.

If there are matches, the closest match is determined at 620. A variety of algorithms and parameters may be employed in determining the closets match. At 622, notification of the closest match is produced with or without identifying the object type. The method 600 may then terminate at 624.

In some embodiments, the method 600 would return control back to 604 in lieu of terminating at 624. For example, some embodiments may attempt to find matches for more than one sequence, at more than one location, and/or at more than one viewpoint or angle. In other embodiments, the method 600 may operate as separate processes or threads, in parallel or concurrently with one another.

Figure 13:
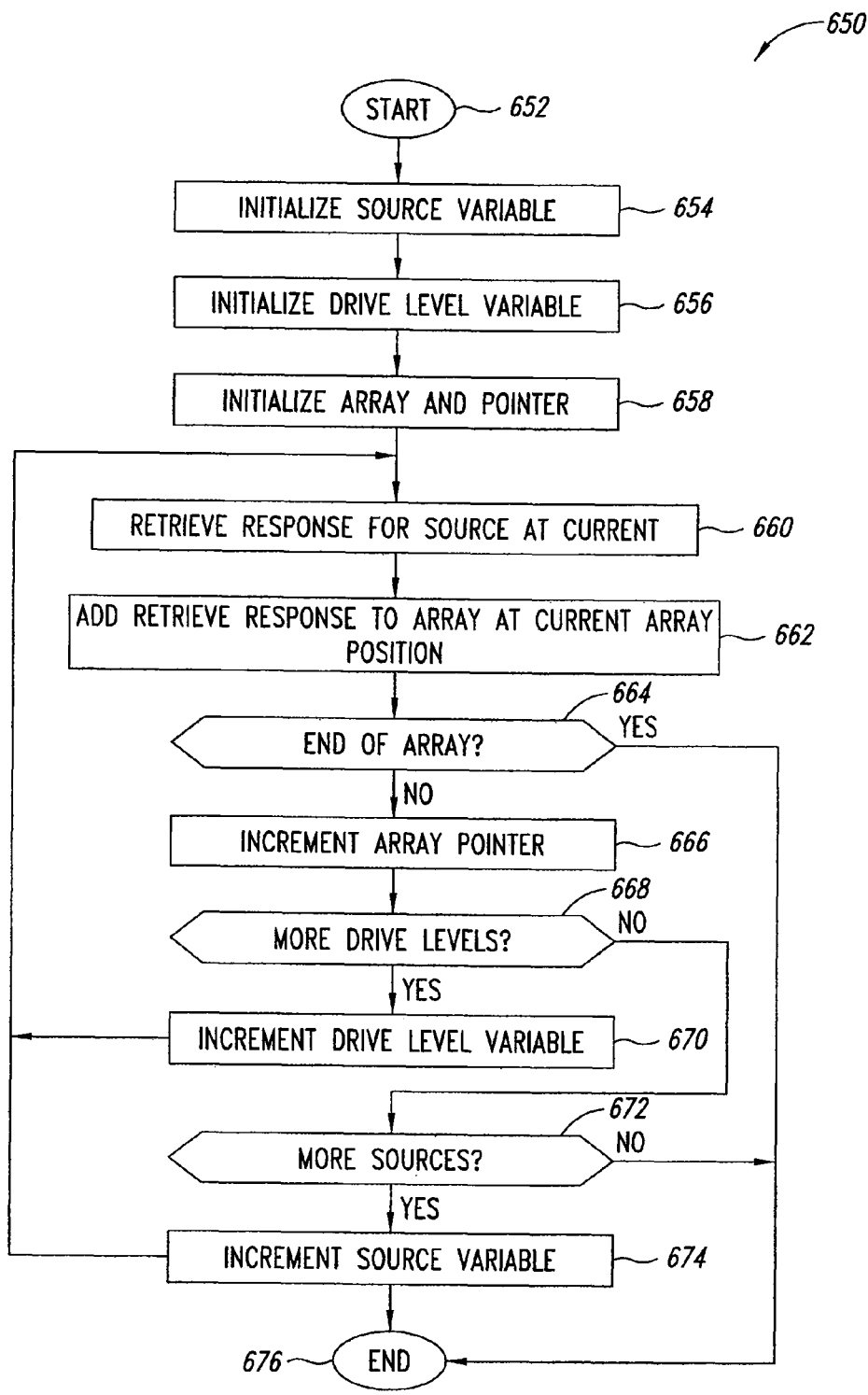
FIG. 13 is a flow diagram showing a method of forming an expected response by an object to a sequence of illumination from stored data representing distinct reference responses to different bands of illumination, according to one illustrated embodiment.

FIG. 13 shows a method 650 of forming an expected reference response for a sequence from a set of discrete reference responses to individual emission bands by an object 50, according to one illustrated embodiment. In some embodiments, the method 650 may be performed or executed by the computing system 18. In other embodiments, the method 650 may be performed or executed by test device 14.

The method 650 starts at 652. For example, the method 650 may start in response to a call from another routine program or process. Alternatively, the method 650 may start in response to a user input or receipt of data or information.

At 654, a source variable is initialized. The source variable may identify a particular source 44 having an emissions spectrum or spectra or may identify the particular emissions spectrum or spectra of the source 44. At 656, a drive level is initialized. For example, the drive level may be initialized to a defined current, voltage, or duty cycle. At 658, an array is initialized. For example, the value of the array, as well as an array pointer, may be initialized.

At 660, a reference response 202 (FIG. 6) by a reference object to illumination by a source identified by the source variable at the defined drive level (e.g., current level) identified by the drive level variable is retrieved. The reference response 202 may be retrieved from a memory or database 20, 34 and, in particular, may be retrieved from a data structure 200 (FIG. 6). At 662, the retrieved reference response 202 is added to the array at the current array position identified by the array pointer.

At 664, it is determined whether the array pointer is pointing at the end of the array. If the array pointer is pointing at the end of the array, the method 650 terminates at 676. If the array pointer is not pointing at the end of the array, control passes to 666 where the array pointer is incremented or decremented.

At 668, it is determined whether there are additional drive levels for the source 44. If there are additional drive levels, the drive level variable is incremented or decremented at 670, and control returns to 660. If there are not additional drive levels, control passes to 672.

At 672, it is determined whether there are additional sources. If there are additional sources, the source variable is incremented or decremented at 674, and control returns to 660.

If there are not additional sources, the method 650 terminates at 676. In some embodiments, the method 650 would return control back to 654 in lieu of terminating at 676. In other embodiments, the method 650 may operate as separate processes or threads, in parallel or concurrently with one another.

Figure 14:
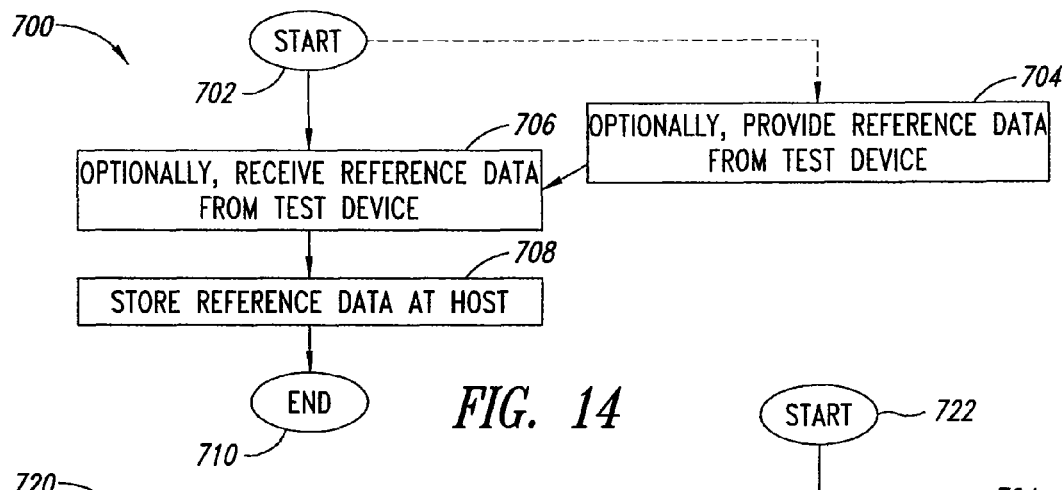
FIG. 14 is a flow diagram showing a method of storing reference data at a host system, according to one illustrated embodiment.

FIG. 14 shows a method of storing reference data at the host evaluation system 18, according to one illustrated embodiment.

The method 700 starts at 702. For example, the method 700 may start in response to a call from another routine program or process. Alternatively, the method 700 may start in response to a user input or receipt of data or information.

Optionally, at 704, reference data is provided to the computing system 18 of the evaluation system 12. The reference data may be provided from one or more of the test devices 14 or computers 26, 32 associated with equipment for capturing the reference data. The reference data may include reference responses which may take the form of responses by reference objects to defined illumination. For example, reference responses may take the form of signals indicative of electromagnetic energy received from an object 50 in response to illumination with a known bandwidth of electromagnetic energy, by a known source 44, at a known drive level (e.g., current, voltage, duty cycle) and/or known temperature.

Optionally, at 706, the computing system 18 receives the reference data. At 708, the computing system 18 stores the reference data. The reference data may be stored in a data structure such as the data structure 200 (FIG. 6). The reference data may be stored in any of a variety of storage mediums, such as storage or database 20 (FIGS. 1-3). While described in terms of storage at the computing system 18, reference data may, alternatively, be stored at the proprietary storage or database 34 (FIG. 3) or even at the remote test device, for example ROM 58 and/or RAM 60 (FIG. 4).

The method 700 terminates at 710. In some embodiments, the method 700 would return control back to 702 in lieu of terminating at 710. In other embodiments, the method 700 may operate as separate processes or threads, in parallel or concurrently with one another.

Figure 15:
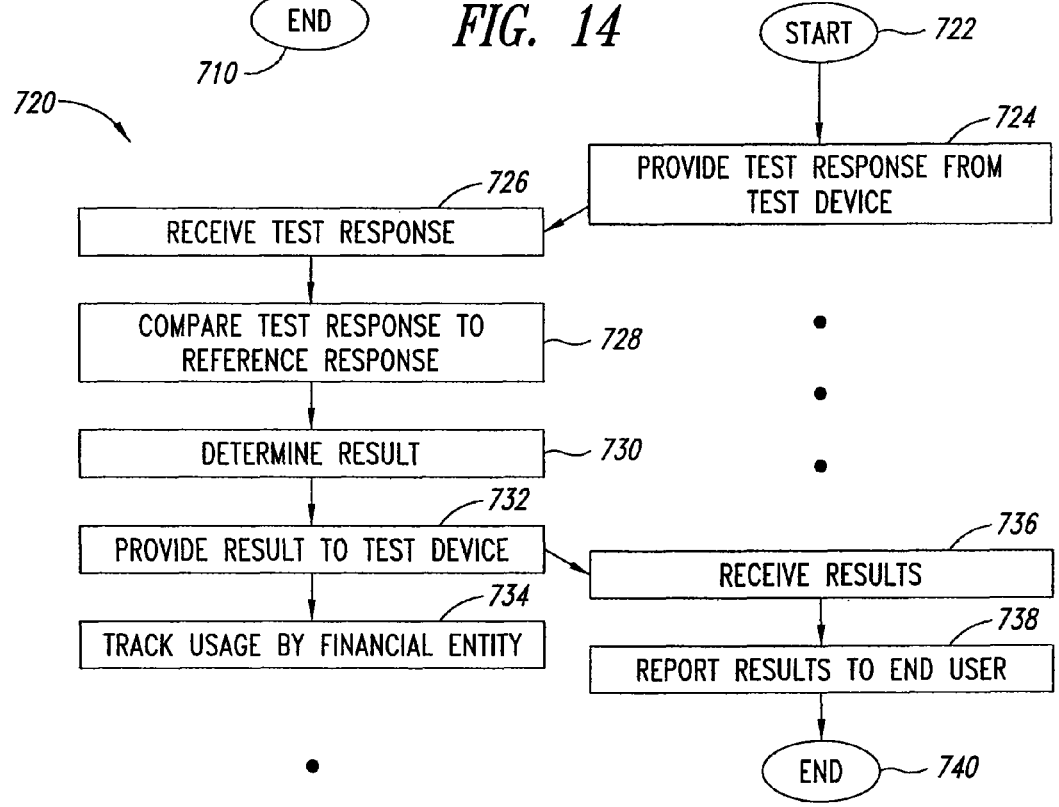
FIG. 15 is a flow diagram showing a method of analyzing test data with respect to the reference data, according to one illustrated embodiment.

FIG. 15 shows a method 720 of operating the evaluation system 18 and test device 14, according to one illustrated embodiment.

The method starts at 722. For example, the method 720 may start in response to activation or turning on of the test device 14. Alternatively, the method 720 may start in response to a user input, receipt of data, or signal received from a sensor.

At 724, the test device 14 provides a test response to the computing system 18.

At 726, the computing system 18 receives the test response. At 728, the computing system 18 compares the test response to a reference response. At 730, the computing system 18 determines a result of the comparison. At 732, the computing system 18 provides the result to the test device 14. At 734, the computing system 18 or associated separate accounting system (not shown) tracks usage by a financial entity, such as a business (e.g., corporation, partnership, sole proprietorship, limited liability company), a division of a business, a non-profit, a government (e.g., federal, state or provincial, county or parish, city or town), of division of a government (e.g., agency, department)). The financial entity is an entity financially obligated for the various transactions occurring on the evaluation system 10. The financial entity may, for example, be the owner, operator, lessee, or otherwise in control of test devices 14 and/or database 20, 34.

At 736, the test device 14 receives the results. At 738, the test device 14 reports the results to the end user, for example, via one of the elements 68, 70 of the user interface.

The method 720 terminates at 740. In some embodiments, the method 720 would return control back to 722 in lieu of terminating at 740. In other embodiments, the method 720 may operate as separate processes or threads, in parallel or concurrently with one another.

Figure 16:
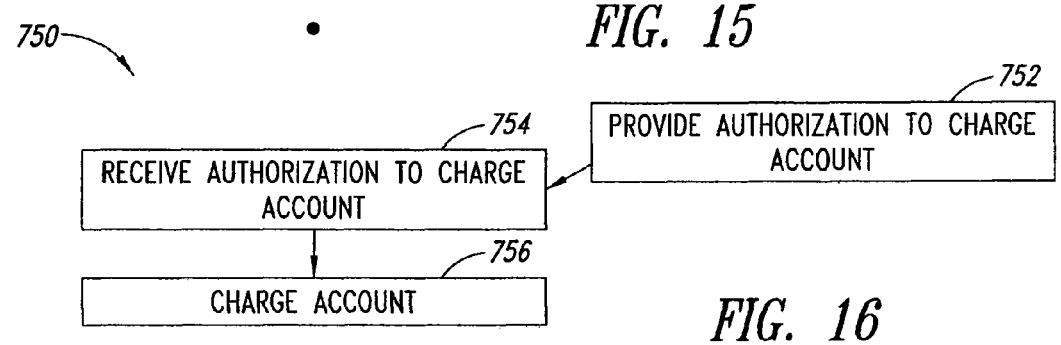
FIG. 16 is a flow diagram showing a method of executing a financial transaction, according to one illustrated embodiment.

FIG. 16 shows a method 750 of tracking financial usage by a financial entity, according to one illustrated embodiment.

At 752, a test device 14 may provide authorization to charge an account to the computing system 18 or associated separate accounting system (not shown). At 754, the computing system 18 or associated separate accounting system receives the authorization to charge the account. At 756, the computing system 18 or associated separate accounting system charges the account. It is noted that the accounting system may in some embodiments be implement on or as part of the computing system 18, which as previously noted as including one or more computer or computing systems.

FIG. 17 shows a method 760 of executing a financial transaction, according to one illustrated embodiment. At 762, the computing system 18 reports charges to the financial entity.

FIG. 18 shows a method 766 of executing a financial transaction, according to another illustrated embodiment. At 768, the computing system 18 charges an account associated with a financial entity on a per-use basis. A use may correspond to the storage of reference data, the receipt of test data, the analysis of test data, and/or the provision of results from analysis of test data.

FIG. 19 shows a method 772 of executing a financial transaction with a financial entity, according to yet another illustrated embodiment. At 774, the computing system 18 charges an account per request received.

FIG. 20 shows a method 778 of executing a financial transaction with a financial entity, according to still another illustrated embodiment. At 780, the computing system 18 charges an account per result provided.

FIG. 21 shows a method 784 of executing a financial transaction with a financial entity, according to even still another illustrated embodiment. At 786, the computing system 18 charges an account of the financial entity on the basis of time. The time may, for example, be indicative of time spent analyzing test responses.

FIG. 22 shows a method 790 of executing a financial transaction with a financial entity, according to a further illustrated embodiment. At 792, the computing system 18 charges an account of the financial entity on a flat-fee basis. The flat-fee charge may be with, or without, excess usage fees.

FIG. 23 shows a method 796 of executing a financial transaction with a financial entity, according to even a further illustrated embodiment. At 798, the computing system 18 charges an account for storage of reference data. The charge may be a one-time fee and/or a periodic fee (hourly, daily, monthly, yearly, etc.). The charge may be based on the number of transactions or elements. Additionally, or alternatively, the charge may be based on the size of storage required.

Figure 24:
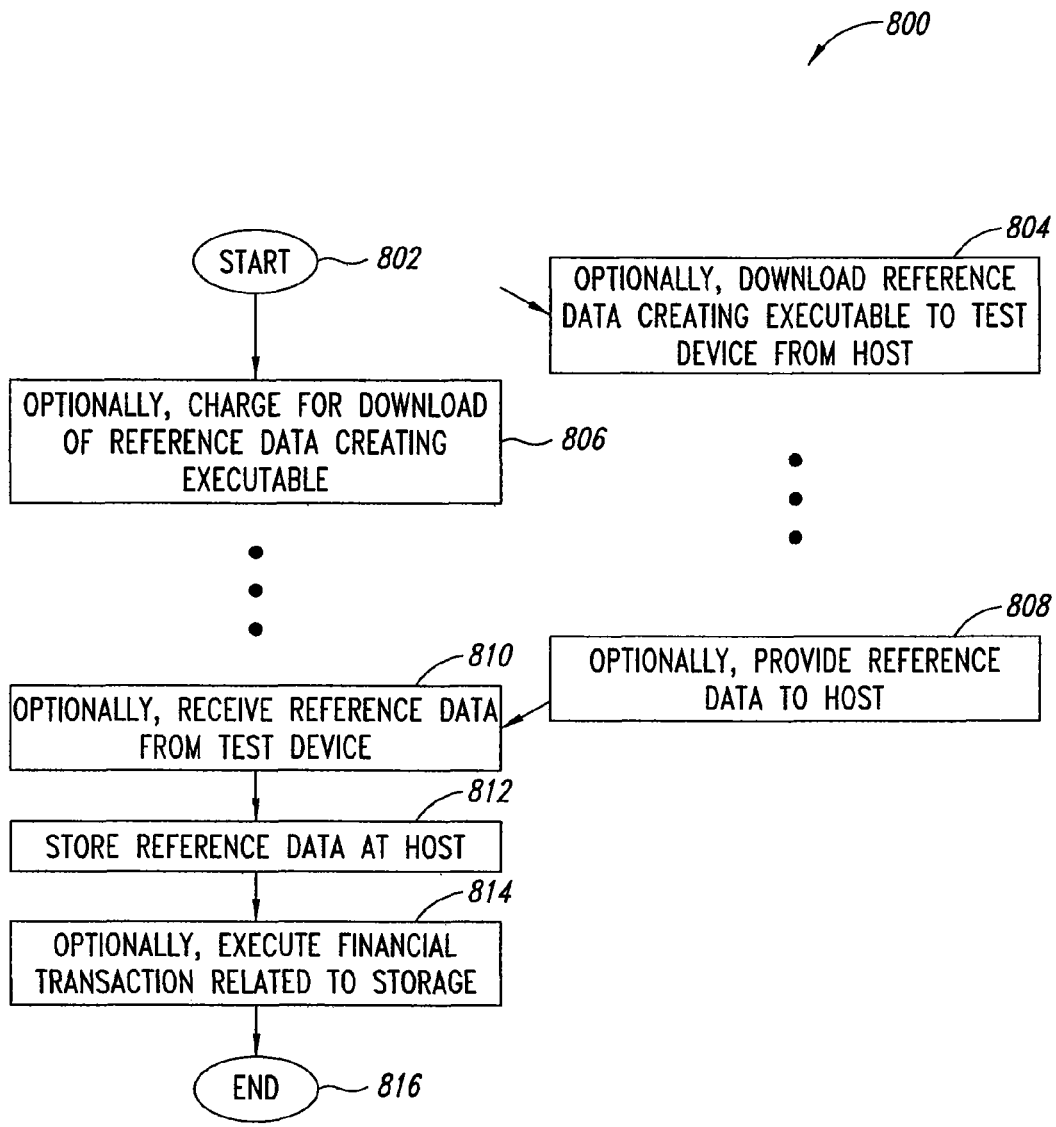
FIG. 24 is a flow diagram showing a method of transferring executable modules and data between the host system and remote test device, according to an illustrated embodiment.

FIG. 24 shows a method 800 of operating test devices 14 in test evaluation system 18, according to another illustrated embodiment.

The method starts at 802. For example, the method may start in response to the starting or powering up of the test evaluation system 18 or remote device 14. Alternatively, the method 800 may start in response to a user input, receipt of data or instructions or receipt of a signal from a sensor.

Optionally at 804, the test device 14 may download a reference data creating executable module from the computing system 18. The reference data creating executable module provides instructions executable on the test device 14 to cause the test device 14 to create reference data.

Optionally at 806, the test evaluation system 18 or associated accounting system charges the financial entity for the downloading of the reference data creating executable module.

Optionally, at 808, the remote device 14 provides reference data to the computing system 18.

Optionally at 810, the computing system 18 receives the reference data from the test device 14. Optionally at 812, the computing system 18 stores the received reference data. For example, the computing system 18 may store the reference data in one of the storage or databases 20a-20d. Optionally at 814, the computing system 18 executes a financial transaction related to the storage of the reference data.

The method 800 terminates at 816. In some embodiments, the method 800 would return control back to 802 in lieu of terminating at 816. In other embodiments, the method 800 may operate as separate processes or threads, in parallel or concurrently with one another.

Figure 25A:
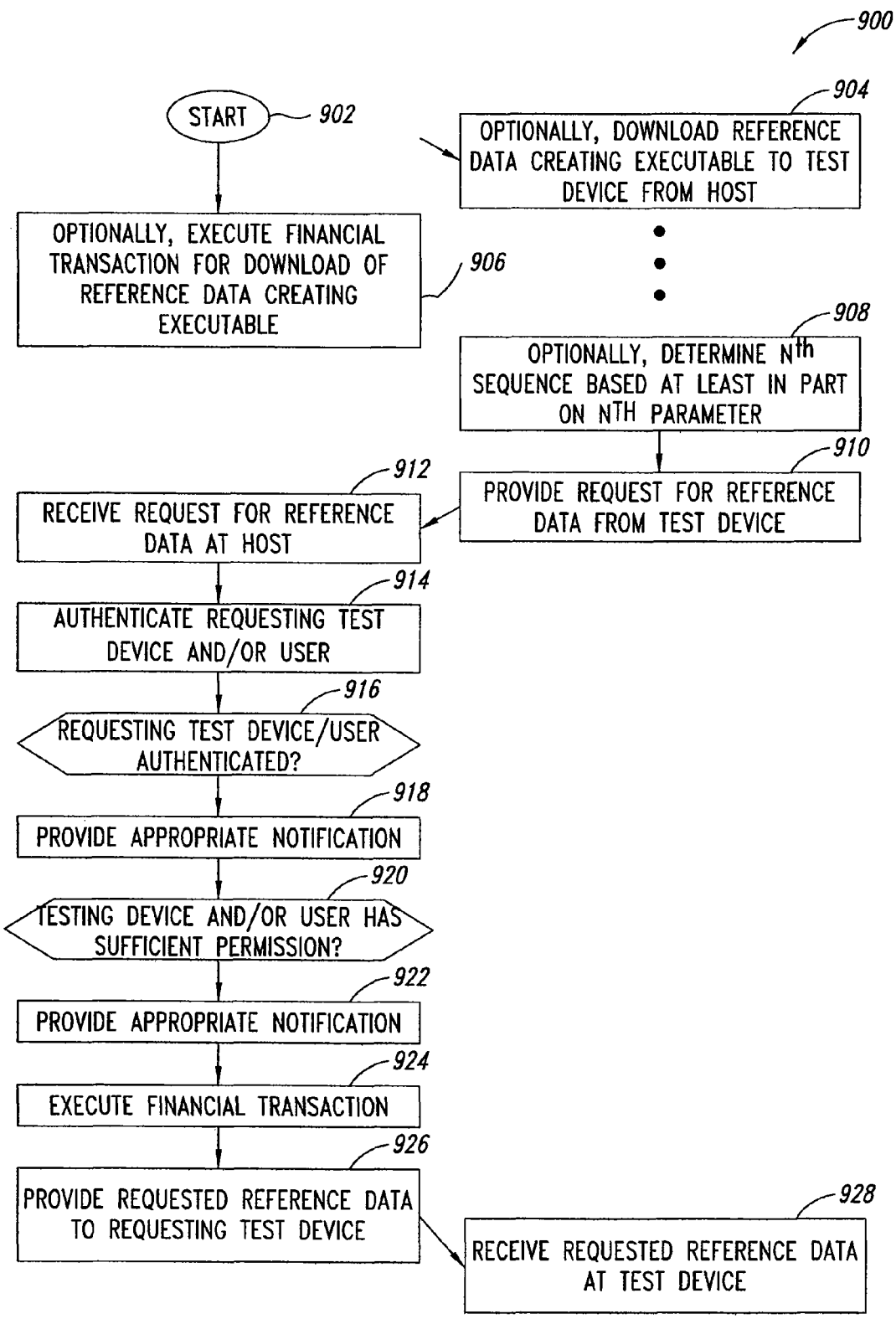
FIGS. 25A and 25B are a flow diagram showing a method of transferring executable modules and data between the host system and remote test device, according to another illustrated embodiment.
Figure 25B:
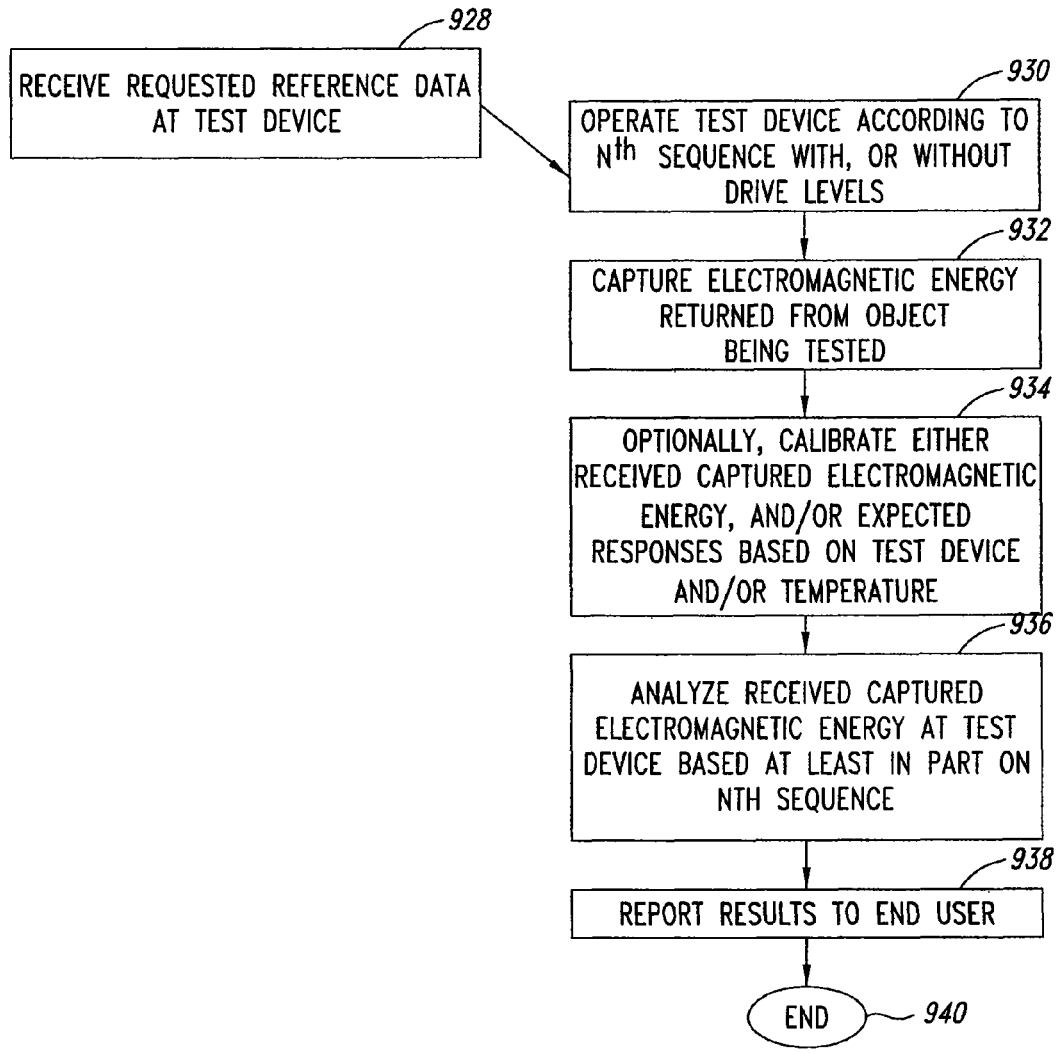

FIGS. 25A and 25B show a method 900 of operating computing system 18 of the host system 12 and the test devices 14, according to yet another illustrated embodiment.

The method 900 starts at 902. For example, the method may start in response to activation or powering of the test device 14 and/or host evaluation system 18. Alternatively, the method 900 may start in response to a user input, receipt of data or instructions, or receipt of a signal from a sensor.

Optionally at 904, the test device 14 downloads a test data creating executable module from the computing system 18. The test data creating executable module provides instructions executable on the test device 14 to cause the test device 14 to create test data, including test responses by objects 50 (FIG. 4) being tested or otherwise evaluated. This may allow the test device 14 to be upgraded as new software and/or hardware is developed. Optionally, at 906, the computing system 18 or associated accounting system executes a financial transaction with a financial entity for the download of the test data creating executable module. Various approaches to executing financial transactions were discussed above in reference to FIGS. 15-24, and will not be repeated in the interest of brevity and clarity. Optionally, at 908, the test device 14 determines an $N^{th}$ sequence based at least in part on an $N^{th}$ parameter. Such was discussed above in reference to FIG. 9, and will not be repeated in the interest of brevity and clarity. It is noted that the $N^{th}$ sequence and/or $N^{th}$ parameter indicate a respective one of a plurality of sequences and/or parameters, whether or not those sequences and/or parameters are based on an indication of time. At 910, the test device 14 provides a request for reference data to the computing system 18.

At 912, the computing system 18 receives the request for reference data. At 914, the computing system 18 authenticates the requesting test device 14 and/or user of the requesting test device 14. For example, the computing system 18 may verify a user identifier and/or device identifier. Additionally, or alternatively, the computing system 18 may verify a password and/or personal identification number (PIN). The computing system 18 may employ other approaches to authenticating the test device 14 and/or user. At 916, the computing system 18 determines whether the requesting test device is authenticated. At 918, the computing system 18 provides an appropriate notification. For example, the computing system 18 may provide a notification to the test device 14 indicating whether or not the test device 14 has been authenticated. Additionally, or alternatively, the computing system 18 may provide a warning or other notification of an invalid attempt to access data to appropriate security personnel, and/or create a log of such attempts.

At 920, the computing system 18 determines whether the requesting testing device 14 and/or user of the requesting test device 14 has sufficient permission to access the data. The computing system 18 may check one or more permission data structures to determine a level of access granted to the testing device 14 and/or user of the requesting test device 14. Access may, for example, be limited to data related to certain objects. Alternatively, or additionally, data may be limited to authorized personnel with, for example with respect to identification of individuals and/or bodily tissue. Other restrictions may of course apply. At 922, the computing system 18 provides an appropriate notification. For example, the computing system 18 may provide a notification to the requesting test device 14 indicating whether or not the requesting test device 14 and/or user has sufficient authorization. Additionally, or alternatively, the computing system 18 may provide notification or an alert of an attempt to improperly access data to appropriate security personnel, and/or create a log of such attempts.

At 924, the computing system 18 executes a financial transaction. Examples of such have been discussed previously and will not be repeated here in the interest of brevity. At 926, the computing system 18 provides requested reference data to the requesting test device 14.

At 928, the test device 14 receives the requested reference data. At 930, the test device 14 operates the sources 44 according to the $N^{th}$ sequence with, or without, drive levels. For example, the control subsystem 54 and/or microprocessor 56 may drive the sources 44 in an order, timing and/or drive level defined by the $N^{th}$ sequence.

At 932, the sensor 56 captures the response of the object 50 in the form of electromagnetic energy returned from the object 50 being tested.

Optionally at 934, the test device 14 calibrates either the received captured electromagnetic energy and/or the expected responses. As discussed above, the calibration may be based on temperature and/or specific physical or performance attributes of the specific sources 44, details of which will not be repeated here in the interest of brevity and clarity.

At 936, the test device 14 analyzes received captured electromagnetic energy based at least in part on the $N^{th}$ sequence. Such analysis has been previously discussed with reference to operation of the computing system 18, and will not be repeated. The test device 14 can employ a similar or identical approach. At 938, the test device 14 reports the results to the end user, for example via elements 68, 70 of the user interface.

The method 900 terminates at 940. In some embodiments, the method 900 would return control back to 902 in lieu of terminating at 940. In other embodiments, the method 900 may operate as separate processes or threads, in parallel or concurrently with one another.

Figure 26:
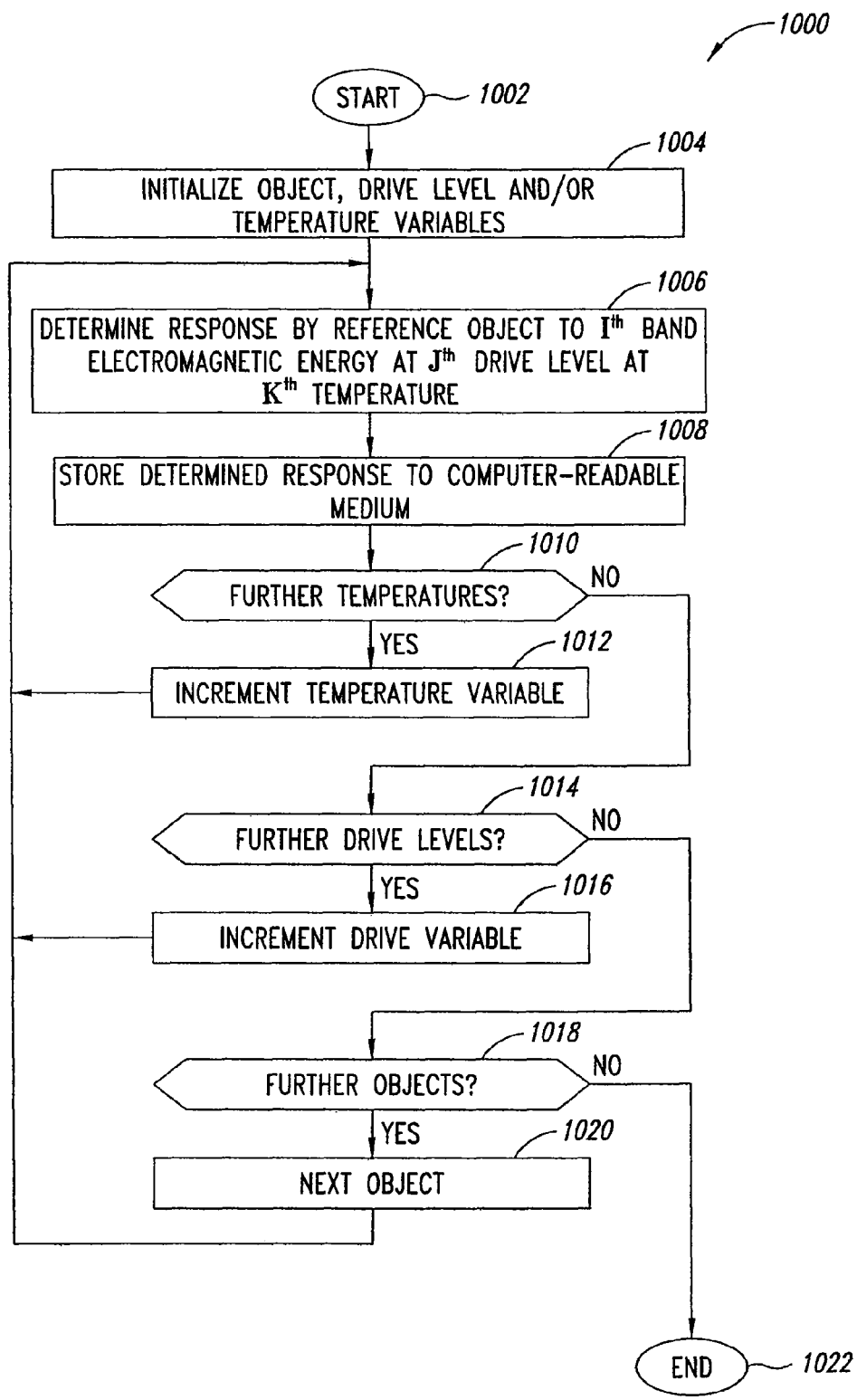
FIG. 26 is a flow diagram showing a method of storing reference data to a data structure, according to one illustrated embodiment.

FIG. 26 shows a method 1000 of operating the computing system 18 and/or test device 14 to create reference data including reference responses, according to one illustrated embodiment.

The method 1000 starts at 1002. For example, the method may start in response to the activation or powering of the computing system 18 and/or test device 14. Alternatively, the method 1000 may start in response to a user input, receipt of data or instructions or receipt of a signal from a sensor.

At 1004, object, drive level, and/or temperature variables are initialized. Initialization permits incrementing through the various variables.

At 1006, a response by a reference object to an $I^{th}$ band electromagnetic energy at $J^{th}$ drive level and/or a $K^{th}$ temperature is determined. The denominations $I^{th}$, $J^{th}$, and $K^{th}$ are used to indicate successive values for the corresponding variables. The drive level may, for example, correspond to a current, voltage, or duty cycle at which the source 44 is operated. The temperature may correspond to a temperature at which the source 44 is operated or expected to be operated. The creation of reference data may take place in a temperature-controlled environment such that the temperature can be incremented for collecting of reference data at various temperature intervals. Various specimens of an object or different objects may be employed to collect the reference responses.

At 1008, the determined reference response is stored along with related information as reference data to a computer-readable medium. Storage of the reference data was discussed previously, for example in reference to FIG. 14, and is not repeated in the interest of brevity and clarity. As noted above, the computer-readable medium may take the form of a storage medium or database 20, 34, or ROM 58, RAM 60, or other medium.

At 1010, a determination is made whether reference responses and additional reference data will be collected at additional temperatures. If so, the temperature variable is incremented at 1012 and control returns to 1006. If not, control passes to 1014.

At 1014, it is determined whether reference responses and additional reference data will be collected at additional drive levels. If so, the drive level variable is incremented at 1016, and control returns to 1006. If not, control passes to 1018.

At 1018, it is determined whether reference responses and additional reference data, including reference responses, will be collected from further objects. If so, the next object is selected or positioned for illumination at 1020. Control then returns to 1006. If not, the method 1000 terminates at 1022. In some embodiments, the method 1000 would return control back to 1002 in lieu of terminating at 1022. In other embodiments, the method 1000 may operate as separate processes or threads, in parallel or concurrently with one another.

Figure 27:
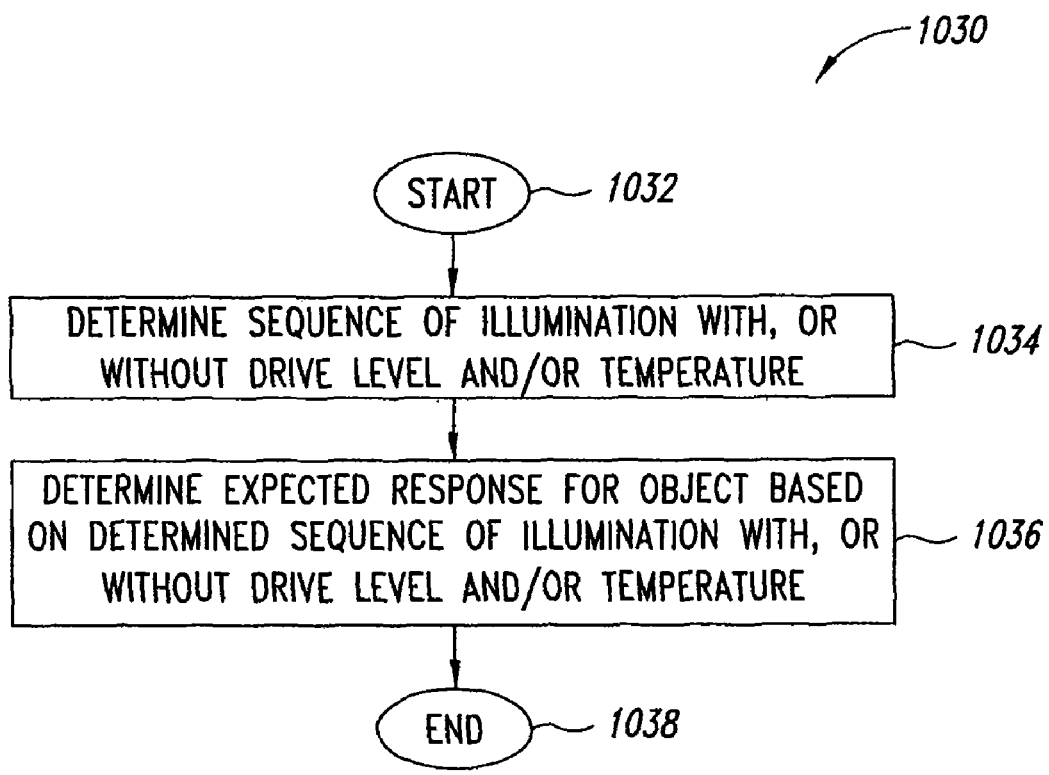
FIG. 27 is a flow diagram showing a method of determining an expected response based on a number of parameters, according to one illustrated embodiment.

FIG. 27 shows a method 1030 of operating the computing system 18 of the host system 12 and/or test device 14, according to a further illustrated embodiment.

The method 1030 starts at 1032. For example, the method 1030 may start in response to activation or powering of the computing system 18 or test device 14. Alternatively, the method 1030 may start in response to a user input, receipt of data or instruction, or receipt of a signal from a sensor.

At 1034, a sequence for driving the sources 44 is determined which may, or may not, include a variety of drive levels. In some embodiments, the sequence may also define a variety of temperatures for the sources 44, where such temperatures can be controlled, for example by one or more heaters such as resistors (not shown) and/or one or more thermoelectric coolers (not shown). As discussed previously, the sequence may include an order for activating individual or groups of the sources 44 or for otherwise causing emission from the various sources 44. The sequence may also include various drive levels for one or more of the sources 44.

At 1036, an expected response for an object 50 (FIG. 4) is determined. The expected response may be determined, based in part, on the determined sequence with, or without specific drive levels, and with, or without temperature levels.

The method 1030 terminates at 1038. In some embodiments, the method 1030 would return control back to 1032 in lieu of terminating at 1038. In other embodiments, the method 1030 may operate as separate processes or threads, in parallel or concurrently with one another.

Figure 28:
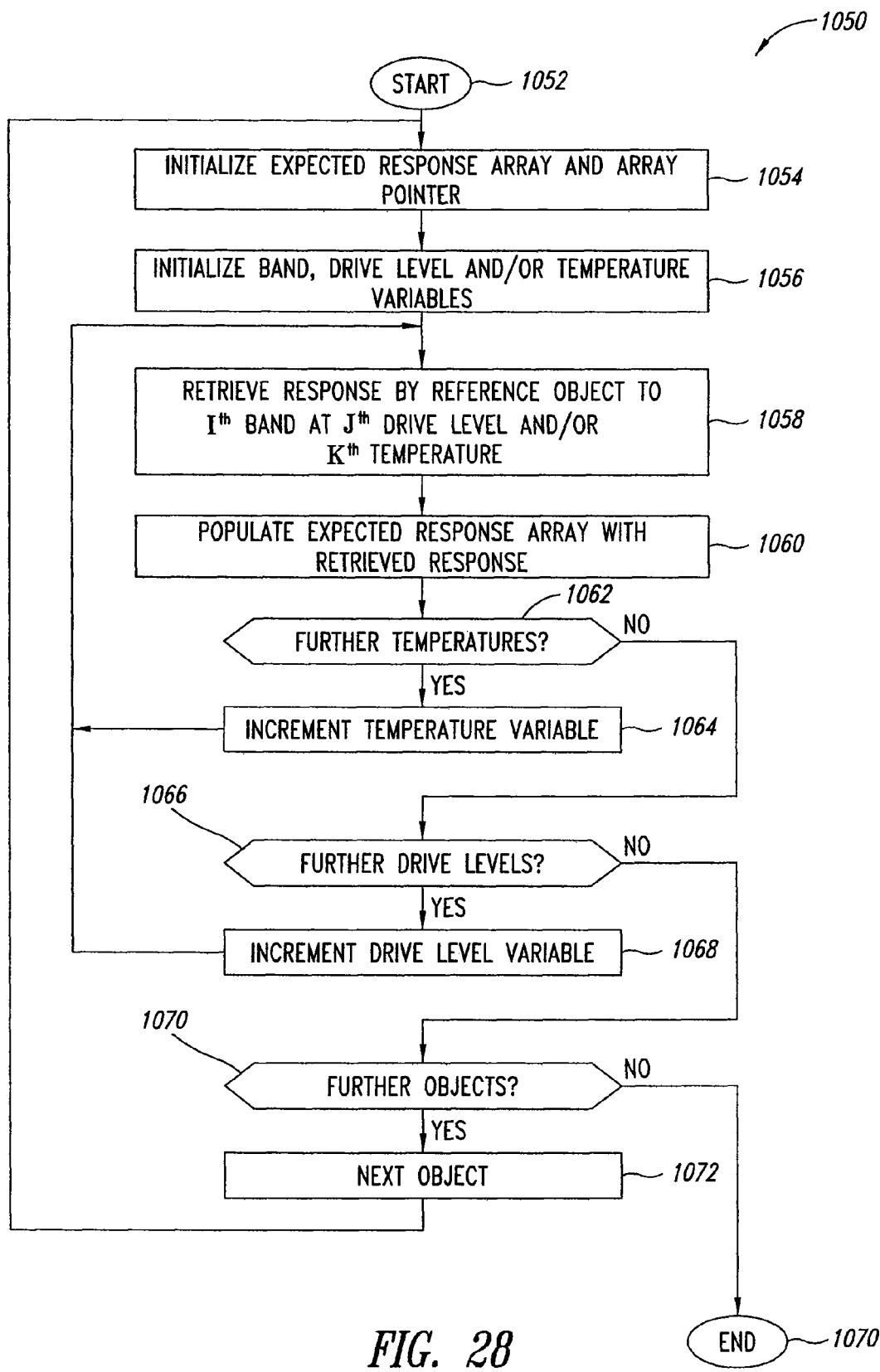
FIG. 28 is a flow diagram showing a method of forming an expected response from stored reference data, according to one illustrated embodiment.

FIG. 28 shows a method 1050 of determining or building an expected response to a sequence from a set or plurality of discrete reference responses, according to one illustrated embodiment. The method 1050 may advantageously reduce storage requirements. For example, reference responses to individual emission spectra may be stored, and a reference response for different sequences built from the individual emission spectra.

The method 1050 starts at 1052. For example, the method 1050 may start in response to activation or powering of the evaluation subsystem 18 and/or the test device 14. Alternatively, the method 1050 may start in response to a user input, receipt of data or instructions, or receipt of a signal from a sensor.

At 1054, an expected response array and array pointer are initialized. At 1056, emission band, drive level, and/or temperatures variables are initialized. At 1058, a response by a reference object to an $I^{th}$ emission band at a $J^{th}$ drive level and/or a $K^{th}$ temperature is retrieved. As discussed previously, the denominations $I^{th}$, $J^{th}$, and $K^{th}$ indicate successive values for the corresponding variables. At 1060, the expected response array is populated with a retrieved response for the given variables.

At 1062, it is determined whether a response at additional temperatures will be determined. If so, the temperature variable is incremented at 1064, and control returns to 1058. If not, control passes to 1066.

At 1066, it is determined whether the expected response will reflect additional drive levels. If so, the drive level variable is incremented at 1068, and control returns to 1058. If not, control passes 1070.

At 1070, it is determined if expected response by further objects will determined. If so, the next object is employed at 1072 and control returns to 1054 where a new expected response array will be created. If not, the method 1050 terminates at 1074. In some embodiments, the method 1050 would return control back to 1052 in lieu of terminating at 1070. In other embodiments, the method 1050 may operate as separate processes or threads, in parallel or concurrently with one another.

In some embodiments, the set of reference data representing responses of various reference objects to at least one sequence of illumination with a plurality of bands of electromagnetic energy may be produced based at least in part on at least one of a standard database of spectral signatures or a set of predicted spectral signatures based one a chemical composition of the reference objects, and a set of spectral characteristics of at least one of a source or a sensor of the remote test device.

EXAMPLES

Example 1

ID/Passport Verification

A pattern database of passport photos of every U.S. citizen may be searchable within seconds to confirm their identity. For security purposes, the search patterns for the entire database may be changed, for example, in less than thirty minutes or even on demand. This may reduce or eliminate identification document fraud, and also reduces or eliminates the cracking the security code.

The object evaluation system 10 can verify a passport or other identification documentation as follows:

When a passport application is submitted, a photo is included which will be affixed to a validly issued passport. The photo identifies the person submitting the application. Once the issuing authority determines that a passport is to be issued, the issuing authority will generate and store at least one known reference pattern associated with the photo (the reference object 50 in this example), as well as other identity information relating to the identity of the person to whom the passport is issued, such as the person's name, physical characteristics, address, social security number, etc. (other issuance information can also be included if necessary, such as for example the date of issuance). A data file containing the reference pattern 202 (FIG. 6) and associated identity information is stored in the data structure 200 with a plurality of other reference patterns 202 generated by the issuing authority for other validly issued passports. The issued passport containing the photo is then sent to the person who submitted the application.

At a security checkpoint, for example at an airport terminal, a passport is provided by a traveler for identification purposes. The passport (sampled object 50) is provided to the test device 14 of the system 10. A region is selected within the passport photo (the sampled object 50 in this example) for which a spectrum measuring device of the test device 14 measures the spectral contents, i.e., color information, and outputs information indicative of the same to the computing system 18 or microprocessor 56 operating spatial analysis software.

The spectral content information outputted by the spectrum measuring device is provided as input to the spatial analysis software program, which generates a measured pattern for the sampled passport photo. In some embodiments, the measured pattern may be in the XYZ color space, and/or the measured pattern can be observed from virtually any angle. The measure pattern (or a view key generated therefrom) is compared to the plurality of reference patterns stored in the passport issuing authority's database (or view keys generated therefrom) until a matching reference pattern is found. If a matching reference pattern is not found, then the passport is deemed to be a fraud by the spatial analysis software. If a match is located, identity information associated with the matching reference pattern is analyzed to determine if the identity information for the matching reference pattern substantially corresponds to the identity information associated with the sampled passport photo.

At least a portion of the identity information associated with the sampled passport photo is generally located within the passport, and can be provided to the spatial analysis software for analysis (e.g., by the user entering or scanning the identity information present in the passport), and/or the identity information within the passport can be provided to the human user to perform the comparison. If the identity information associated with the sampled passport photo matches the identity information associated with the matching reference pattern, the passport photo will be deemed an authentic and validly issued passport (i.e., not a forgery) by the spatial analysis software, and the traveler will be permitted to proceed past the security checkpoint.

Further, it should be understood that the materials used to construct the passport (or other identification documentation materials) can be validated against known spectral or color data. The paper and inks can be checked to determine if the passport itself is a forgery, not just the photo or information printed on the document.

Example 2

Document Authentication

The object evaluation system 10 can be used to detect forgeries of a document of value, such as money or bank notes, or other sensitive documents operates as follows:

When a document is validly produced, the producing entity generates and stores at least one reference pattern 202 for the original document (the reference object 50 in this example), as well as other identity information relating to the identity or characteristics of the document, such as the date it was produced, a general title for the document, key terms or monetary value, etc. A data structure 200 containing the reference pattern 202 and identity information associated with the reference pattern 202 is then delivered or made available to an eligible recipient of the original document.

When the recipient is later presented with a document (sampled object 50), the recipient can use the object evaluation system 10 to check the authenticity of the presented document, i.e., to determine whether the presented document is the original document or of the same quality or origin as the original document. It should be understood that if the document is one that is duplicated, such as a dollar bill for example, then only reference patterns for one representative document needs to be used for authentication.

The presented document is provided to a spectrum measuring device of the test device 14. A region is selected within the presented document (the sampled object 50 in this example) for which the spectrum measuring device measures the spectral content and outputs information indicative of the same to the computing system 18 or microprocessor 56 operating spatial analysis software.

The spectral content information outputted by the spectrum measuring device is provided as input to the spatial analysis software, which generates a measured pattern for the sampled document. The measured pattern (or a view key generated therefrom) is compared to the specific reference pattern 202 previously generated for the original document (or a view key generated therefrom). If the measured pattern does not match the reference pattern 202, then the presented document is deemed a forgery by the spectral analysis software. If the measured pattern matches the reference pattern, then the presented document is deemed authentic by the spectral analysis software and the recipient can accept the presented document.

For further authentication, the identity information associated with the original document can also be compared to identity information associated with the presented document to determine if they substantially correspond. At least a portion of the identity information associated with the presented document is generally located within the document, and can be provided to the spatial analysis software for analysis (e.g., by the user entering or scanning the identity information present in the document), and/or the identity information within the presented document can be provided to the human user to perform the comparison.

Example 3

Product Monitoring

The object evaluation system 10 can be used for brand protection to verify the authenticity of a product based on the make of its material (e.g., fabric colors) operates as follows:

When a manufacturer mass produces a product, at least one reference pattern 202 for a representative of the product (the reference object 50 in this example) is generated and stored in the reference pattern data structure 200, as well as identity information associated with the original product, such as the name or style of the product, a serial number, a color description, a size, the manufacturer's name and address, etc.

To determine if the product (sampled object 50) is of the same quality or of the same origin as the original representative product, a distributor or individual consumer can provide the product to be sampled to the object evaluation system 10. A region is selected within the sampled product (the sampled object 50 in this example) for which a spectrum measuring device of the test device 14 measures the spectral content and outputs information indicative of the same to the computing system 18 or microprocessor 56 operating spatial analysis software.

The spectral content information outputted by the spectrum measuring device is provided as input to the computing system 18 or microprocessor 56 executing the spatial analysis software, which generates a measured pattern for the sampled product 50. The measured pattern (or a view key generated therefrom) is compared to the reference patterns 202 in the data structure 200 (or view keys generated therefrom) until a matching reference pattern 202 is found. If a matching reference pattern is not found, then the sampled product 50 is deemed to be a fraud. If a match is located, then the identity information associated with the matching reference pattern is analyzed to determine if the identity information for the matching reference pattern substantially corresponds to the identity information associated with the sampled product. At least a portion of the identity information associated with the sampled product 50 is generally located on a label or tag on the product, or observable by a human user, and can be provided to the computing system 18 or microprocessor 56 executing the spatial analysis software for analysis (e.g., by the user entering or scanning the identity information present in the label or tag or obtained from observation), and/or the identity information associated with the matching reference pattern can be provided to the human user to perform the comparison. If the identity information associated with the sampled product 50 matches the identity information associated with the matching reference pattern, the sampled product 50 will be deemed authentic and the purchase and/or distribution of the sampled product 50 can proceed. If the measured pattern does not match the reference pattern 202, then the sampled product 50 is deemed a knock-off or tampered product.

Thus, the object evaluation system 10 can be utilized for brand protection to verify the authenticity of products based on the make of their fabric colors with the pattern of the original product in database, the system 10 can compare a knock off versus the real product in a matter of minutes by scanning any area of the product for which a database pattern exists. In a preferred embodiment, once the fabric has been scanned, a view key is selected to obtain a pattern file. This pattern file will be compared against a pattern from an authentic fabric sample on our database from the same view key point.

Art forgery is another area of product verification that the object evaluation system 10 can be used. That is, spectral data can be taken from one or more regions of a valuable piece of art and this spectral data could be used to authenticate copies or unknown works.

Quality Control of Manufacturing Process

The object evaluation system 10 can be also be used for quality control of manufacturing processes to maintain quality control on practically any manufactured good or the packaging for the good. In this regard, the system 10 would operate as follows:

When a manufacturer mass produces a product, a variety of reference patterns 202 can be taken from the product (reference object 50) at different locations or areas within the manufacturing process. To determine if the manufacturing process is operating properly, readings can be taken from the products (sampled objects 50) during actual manufacturing and compared to the reference patterns 202 to determine whether the manufacturing process is operating to predetermined quality control standards. Depending upon the results of the comparison, the manufacturing process can be shut down or modified (if the comparison shows unacceptable quality control) or subsequent parts of the manufacturing process can be actuated. For example, if the product (sampled object 50) was a loaf of bread being baked within an oven, then readings could be taken of the loaf of bread and compared with the reference patterns 202 until the comparisons indicate the loaf of bread is ready to be removed from the oven.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems for recognizing, identifying, verifying, authenticating, classifying, and/or diagnosing or otherwise evaluating objects such as, but not limited to, manufactured goods and articles; media, for example identity documents, financial instruments, legal documents, other documents and other media; and biological tissue, not necessarily the exemplary networked evaluation system generally described above.

For example, images of a test object may be useful for more than simple spectral analysis. For instance, the image information may be employed by other image/pattern recognition algorithms to, for example, identify objects independent of, or in conjunction with the test object's spectral composition. Additionally, the image recognition algorithms can usefully interact with the spectral analysis algorithms. For instance, image analysis may be employed to locate a target area within an image of the test object, and carry-out a detailed spectral analysis of the target art. For example, the test device 14 may capture an image of an identification document, such as a passport, at any orientation, find a target area on the identification document (e.g., 3 mm to the left of the lower right hand corner of a photo carried by the passport), and perform a spectral analysis of that target area, which is known to contain particularly useful spectral information. The target area may advantageously be kept confidential to maintain security of the system. In addition to this interaction between spectral analysis and spatial analysis, there can be more complex analyses performed, for example where a signature form a test object comprises a multi-dimensional dataset of spectral information at multiple points in space on the test object.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. Provisional Patent Application Ser. Nos.: 60/623,881, filed Nov. 1, 2004; 60/732,163, filed Oct. 31, 2005; 60/820,938, filed Jul. 31, 2006; 60/834,662, filed Jul. 31, 2006; 60/834,589, filed Jul. 31, 2006; 60/871,639, filed Dec. 22, 2006; 60/883,312, filed Jan. 3, 2007; 60/890,446, filed Feb. 16, 2007; and U.S. Nonprovisional patent application Ser. No. 11/264,626 now abandoned, filed Nov. 1, 2005, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of operating a test device having a control circuit, at least one source, at least one sensor, and at least one communications port, to test objects, the method comprising:

operating the at least one source of the test device by the control circuit of the test device according to a first sequence during a first period to emit electromagnetic energy in a plurality of bands in a first order defined by the first sequence;

capturing electromagnetic energy in at least one part of an optical portion of an electromagnetic spectrum returned to the test device during the first period with the at least one sensor of the test device;

operating the at least one source of the test device by the control circuit according to a second sequence during a second period to emit electromagnetic energy in a plurality of bands in a second order defined by the second sequence, the second sequence different from the first sequence and the second order different from the first order;

capturing electromagnetic energy in at least one part of an optical portion of an electromagnetic spectrum returned to the test device during the second period with the at least one sensor of the test device; and transmitting signals remotely from the test device via the at least one communications port of the test device, the signals indicative of at least one sensed characteristic of the captured electromagnetic energy.

2. The method of claim 1, further comprising:

receiving the first sequence via the at least one communications port of the test device from a host system, the host system remotely located with respect to the test device; and receiving the second sequence via the at least one communications port of the test device from the host system.

3. The method of claim 1, further comprising:

receiving the first sequence in an encrypted form via the at least one communications port of the test device from a host system remotely located with respect to the test device; and receiving the second sequence in an encrypted form via the at least one communications port of the test device from the host system.

4. The method of claim 1, further comprising:

generating the first sequence by the control circuit of the test device;

providing the first sequence to a host system via the at least one communications port of the test device, the host system remotely located with respect to the test device;

generating the second sequence by the control circuit of the test device; and providing the second sequence to the host system via the at least one communications port of the test device.

5. The method of claim 1, further comprising:

generating the first sequence by the control circuit of the test device;

providing the first sequence in an encrypted form to a host system via the at least one communications port of the test device, the host system remotely located with respect to the test device;

generating the second sequence by the control circuit of the test device; and providing the second sequence in an encrypted form to the host system via the at least one communications port of the test device.

6. The method of claim 1, further comprising:

selecting the first sequence by the control circuit of the test device based on a parameter that includes a representation of a first time; and selecting the second sequence by the control circuit of the test device based on a parameter that includes a representation of a second time, different than the first time.

7. The method of claim 6, further comprising:

providing an indication of the first time via the at least one communications port of the test device along with a representation of the captured electromagnetic energy returned to the test device during the first period to a host system remotely located with respect to the test device; and providing an indication of the second time via the at least one communications port of the test device along with a representation of the captured electromagnetic energy returned to the test device during the second period to the host system.

8. The method of claim 1 wherein operating at least one source of the test device according to a first sequence during a first period to emit electromagnetic energy in a plurality of bands includes selectively turning respective ones of a plurality of sources ON and OFF in an order defined by the first sequence.

9. The method of claim 8 wherein selectively turning respective ones of the sources ON and OFF in an order defined by the first sequence includes selectively applying current at a plurality of different levels to respective ones of the sources, where the order and the level is defined by the first sequence.

10. The method of claim 1 wherein operating at least one source of the test device by the control circuit according to a first sequence during a first period to emit electromagnetic energy in a plurality of bands includes selectively applying drive signals at a plurality of different levels to the at least one source in the order defined by the first sequence.

11. The method of claim 1 wherein operating at least one source of the test device by the control circuit according to a first sequence during a first period to emit electromagnetic energy in a plurality of bands includes selectively applying temperature signals at a plurality of different levels to at least one temperature control element proximate the at least one source in the order defined by the first sequence.

12. The method of claim 1, further comprising:

receiving via the at least one communications port of the test device a number of determined authentication results from a host authentication system remotely located from the test device.

13. The method of claim 12 wherein receiving via the at least one communications port of the test device a number of determined authentication results from a host authentication system remotely located from the test device includes receiving at least one authentication result based on a comparison of the electromagnetic energy captured by the at least one sensor of the test device test data with a set of object authentication reference data for a defined reference object.

14. The method of claim 1, further comprising:

transmitting authentication information via the at least one communications port of the test device to a host authentication system remotely located from the test device for use in determining if the test device has a sufficient level of authority.

15. The method of claim 1, further comprising:

transmitting financial transaction information via the at least one communications port of the test device to a host authentication system remotely located from the test device.

* * * * *